United States Patent
Mejia Oneto et al.

(10) Patent No.: US 10,130,723 B2
(45) Date of Patent: Nov. 20, 2018

(54) TCO CONJUGATES AND METHODS FOR DELIVERY OF THERAPEUTIC AGENTS

(71) Applicants: The Regents of the University of California, Oakland, CA (US); The Research Foundation for the State University of New York, Albany, NY (US)

(72) Inventors: Jose Manuel Mejia Oneto, Oakland, CA (US); Maksim Royzen, Albany, NY (US)

(73) Assignees: The Regents of the University of California, Oakland, CA (US); The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 15/382,402

(22) Filed: Dec. 16, 2016

(65) Prior Publication Data

US 2017/0095580 A1    Apr. 6, 2017

Related U.S. Application Data

(63) Continuation of application No. 15/265,158, filed on Sep. 14, 2016, which is a continuation of application No. PCT/US2015/020718, filed on Mar. 16, 2015.

(60) Provisional application No. 62/083,022, filed on Nov. 21, 2014, provisional application No. 62/013,994, filed on Jun. 18, 2014, provisional application No. 61/953,294, filed on Mar. 14, 2014.

(51) Int. Cl.
| | |
|---|---|
| *A61K 51/06* | (2006.01) |
| *A61K 38/14* | (2006.01) |
| *C07D 257/08* | (2006.01) |
| *A61K 47/48* | (2006.01) |
| *A61K 49/00* | (2006.01) |
| *A61K 51/04* | (2006.01) |
| *C07D 311/82* | (2006.01) |
| *C07D 499/74* | (2006.01) |
| *C07H 7/02* | (2006.01) |
| *C07H 15/24* | (2006.01) |
| *C07H 19/167* | (2006.01) |
| *C07H 19/213* | (2006.01) |
| *A61K 31/43* | (2006.01) |
| *A61K 31/7076* | (2006.01) |
| *A61K 38/12* | (2006.01) |
| *A61K 51/12* | (2006.01) |

(52) U.S. Cl.
CPC ............ *A61K 51/065* (2013.01); *A61K 31/43* (2013.01); *A61K 31/7076* (2013.01); *A61K 38/12* (2013.01); *A61K 38/14* (2013.01); *A61K 47/4823* (2013.01); *A61K 47/48023* (2013.01); *A61K 47/48038* (2013.01); *A61K 47/48061* (2013.01); *A61K 47/48353* (2013.01); *A61K 47/48784* (2013.01); *A61K 49/0041* (2013.01); *A61K 49/0043* (2013.01); *A61K 49/0052* (2013.01); *A61K 49/0054* (2013.01); *A61K 49/0073* (2013.01); *A61K 51/0482* (2013.01); *A61K 51/0495* (2013.01); *A61K 51/1213* (2013.01); *C07D 257/08* (2013.01); *C07D 311/82* (2013.01); *C07D 499/74* (2013.01); *C07H 7/02* (2013.01); *C07H 15/24* (2013.01); *C07H 19/167* (2013.01); *C07H 19/213* (2013.01)

(58) Field of Classification Search
CPC ................ A61K 38/14; A61K 49/0073; A61K 47/48353; A61K 49/0041; A61K 49/0054; A61K 51/0482; A61K 51/065; A61K 47/4823; A61K 47/48061; A61K 47/48038; A61K 47/48023; A61K 51/1213; A61K 31/7076; A61K 31/43; A61K 49/0052; A61K 47/48784; A61K 38/12; A61K 49/0043; C07H 7/02; C07H 15/24; C07H 19/167; C07H 19/213; C07D 311/82; C07D 499/74; C07D 257/08

See application file for complete search history.

(56) References Cited

U.S. PATENT DOCUMENTS

| | | | |
|---|---|---|---|
| 5,770,229 | A | 6/1998 | Tanihara et al. |
| 8,552,183 | B2 | 10/2013 | Wiessler et al. |
| 9,421,274 | B2 | 8/2016 | Robillard et al. |
| 9,463,256 | B2 | 10/2016 | Lub et al. |

(Continued)

FOREIGN PATENT DOCUMENTS

| | | |
|---|---|---|
| EP | 1867638 A1 | 12/2007 |
| EP | 2719400 A2 | 4/2014 |

(Continued)

OTHER PUBLICATIONS

Niska et al., Antimicrobial Agents and Chemotherapy, vol. 57, No. 10., 5080-5086, Oct. 2013.*

(Continued)

*Primary Examiner* — Robert S Cabral
(74) *Attorney, Agent, or Firm* — Mintz, Levin, Cohn, Ferris, Glovsky and Popeo, P.C.

(57) ABSTRACT

The present invention provides a method for selective delivery of a therapeutic or diagnostic agent to a targeted organ or tissue by implanting a biocompatible solid support in the patient being linked to a first binding agent, and administering a second binding agent to the patient linked to the therapeutic or diagnostic agent, such that the therapeutic or diagnostic agent accumulates at the targeted organ or tissue.

19 Claims, 23 Drawing Sheets

(56) References Cited

U.S. PATENT DOCUMENTS

| | | |
|---|---|---|
| 2005/0014197 A1 | 1/2005 | Agnew et al. |
| 2009/0023916 A1 | 1/2009 | Fox et al. |
| 2011/0223257 A1 | 9/2011 | Zhao et al. |
| 2011/0268654 A1 | 11/2011 | Hilderbrand et al. |
| 2012/0034161 A1 | 2/2012 | Robillard et al. |
| 2012/0076727 A1 | 3/2012 | McBride et al. |
| 2013/0281644 A1 | 10/2013 | Kiessling et al. |
| 2014/0199331 A1 | 7/2014 | Robillard et al. |
| 2016/0114046 A1 | 4/2016 | Brudno et al. |
| 2016/0120987 A1 | 5/2016 | Mejia Oneto et al. |
| 2017/0087258 A1 | 3/2017 | Oneto et al. |

FOREIGN PATENT DOCUMENTS

| | | |
|---|---|---|
| WO | WO-03/000708 A1 | 1/2003 |
| WO | 2010/051530 A2 | 5/2010 |
| WO | 2011/127149 A1 | 10/2011 |
| WO | 2012/012612 A2 | 1/2012 |
| WO | 2012/049624 A1 | 4/2012 |
| WO | 2012/074840 A2 | 6/2012 |
| WO | 2012/085789 A1 | 6/2012 |
| WO | 2012/156918 A1 | 11/2012 |
| WO | 2012/156919 A1 | 11/2012 |
| WO | 2012/156920 A1 | 11/2012 |
| WO | 2012/168512 A2 | 12/2012 |
| WO | 2014/065860 A1 | 5/2014 |
| WO | 2014/081299 A1 | 5/2014 |
| WO | 2014/081300 A1 | 5/2014 |
| WO | 2014/081301 A1 | 5/2014 |
| WO | 2014/081303 A1 | 5/2014 |
| WO | 2014/117001 A1 | 7/2014 |
| WO | 2014/138186 A1 | 9/2014 |
| WO | 2014/200767 A1 | 12/2014 |
| WO | 2014/205126 A1 | 12/2014 |
| WO | WO-2014/205126 A1 | 12/2014 |
| WO | 2015/139025 A1 | 9/2015 |
| WO | 2015/154082 A1 | 10/2015 |

OTHER PUBLICATIONS

Hofmann et al., J. Biomed. Mater. Res. A. Sep. 2012; 100(9):251702525.*

Al-Dubai et al., "Biocompatible medical implant materials with binding sites for a biodegradable drug-delivery system," Nanotechnology, Science and Applications, No. 4, 2011, pp. 87-94.

Altin et al., "Fabrication of "Clickable" Hydrogels via Dendron-Polymer Conjugates," Macromolecules, 2010, vol. 43, No. 8, pp. 3801-3808.

Antoci, Jr., et al., "The inhibition of *Staphylococus* epidermidis biofilm formation by vancomycin-modified titanium alloy and implications for the treatment of periprosthetic infection," Biomaterials, 2008, vol. 29, pp. 4684-4690.

Blackman et al., "Tetrazine Ligation: Fast Bioconjugation Based on Inverse-Electron-Demand Diels-Alder Reactivity," J. Am. Chem. Soc., 2008, vol. 130, pp. 13518-13519.

Brudno et al., "In Vivo Targeting through Click Chemistry," Chem. Med. Chem., 2015, vol. 10, pp. 617-620.

Brudno et al., "On-demand drug delivery from local depots," J. Control. Release, 2015, http://dx.doi.org/10.1016/j.jconrel.2015.09.011, 10 pages.

Burdick et al., Acellular Biomaterials: An Evolving Alternative to Cell-Based Therapies, Science Translation Medicine, Mar. 13, 2013, vol. 5, Issue 176, 4 pages.

Chung et al., "Ubiquitous Detection of Gram-Positive Bacteria with Bioorthogonal Magnetofluorescent Nanoparticles," ASC NANO, 2011, vol. 5, No. 11, pp. 8834-8841.

Coviello et al., "Polysaccharide hydrogels for modified release formulations," Journal of Controlled Release, 2007, vol. 119, pp. 5-24.

Deforest et al., "Sequential click reactions for synthesizing and patterning three-dimensional cell microenvironments," Nature materials: Letters, Aug. 2009, vol. 8, pp. 659-664.

Desai et al., "Versatile click alginate hydrogels crosslinked via tetrazineenorbornene chemistry," Biomaterials, 2015, vol. 50, pp. 30-37.

Devaraj et al., "Fast and Sensitive Pretargeted Labeling of Cancer Cells through a Tetrazine/trans-Cyclooctene Cycloaddition," Angew. Chem. Int. Ed., 2009, vol. 48, pp. 7013-7016.

Devaraj et al., "Reactive polymer enables efficient in vivo bioorthogonal chemistry," PNAS, Mar. 27, 2012, vol. 109, No. 13, pp. 4762-4767.

Eckhouse et al., "Local Hydrogel Release of Recombinant TIMP-3 Attenuates Adverse Left Ventricular Remodeling After Experimental Myocardial Infarction," Science Translation Medicine, Feb. 12, 2014, vol. 6, Issue 223, 10 pages.

Eschenhagen et al., "Physiological aspects of cardiac tissue engineering," Am. J. Physiol. Heart Circ. Physiol., vol. 30, 2012, pp. H133-H143.

European Application No. 14813532.0, Extended European Search Report dated Dec. 2, 2016, 10 pages.

International Application No. PCT/US2015/020718, "International Search Report and Written Opinion", dated Jun. 10, 2015, 8 pages.

International Application No. PCT/US2014/043020, International Search Report and Written Opinion, dated Oct. 6, 2014, 9 pages.

Kharkar et al., "Designing degradable hydrogels for orthogonal control of cell microenvironments," Chem. Soc. Rev., Sep. 7, 2013, 42(17), pp. 7335-7372; doi:10.1039/c3cs60040h.

Koo et al., "Bioorthogonal Copper-Free Click Chemistry In Vivo for Tumor-Targeted Delivery of Nanoparticles," Angew. Chem. Int. Ed., 2012, vol. 51, pp. 11836-11840.

Koshy et al., "Click-Crosslinked Injectable Gelatin Hydrogels," Advanced Healthcare Materials, 2016, DOI: 10.1002/adhm.201500757, 7 pages.

Landa et al., "Effect of Injectable Alginate Implant on Cardiac Remodeling and Function After Recent and Old Infarcts in Rat," Circulation, Mar. 18, 2008, vol. 17, pp. 1388-1396.

Li et al., "Diels-Alder reaction-triggered bioorthogonal protein decaging in living cells," Natural Chemical Biology, Advanced Online Publication, Nov. 2, 2014, DOI:10.1038/NCHEMBIO.1656.

Li et al., "Monodispersed PEG-DOT A Conjugated Anti-TAG-72 Diabody Has Low Kidney Uptake and High Tumor to Blood Ratios Resulting in Improved $^{64}$Cu PET Imaging," J. Nucl. Med., Jul. 2010, 51(7), pp. 1139-1146; doi:10.2967/jnumed.109.074153.

Matikonda et al., "Bioorthogonal prodrug activation driven by a strain-promoted 1,3-dipolar cycloaddition," Chem. Sci., 2015, vol. 6, pp. 1212-1218.

Mejia Oneto et al., "Implantable biomaterial based on click chemistry for targeting small molecules," Acta Biomaterialia, 2014, vol. 10, pp. 5099-5105.

Neves et al., "Imaging Cell Surface Glycosylation in Vivo Using "Double Click" Chemistry," Bioconjugate Chem., May 5, 2013, vol. 24, pp. 934-941.

Patterson et al., "Finding the Right (Bioorthogonal) Chemistry," ACS Chem. Biol., 2014, vol. 9, pp. 592-605.

Pretze et al., "Recent Trends in Bioorthogonal Click-Radiolabeling Reactions Using Fluorine-18", Molecules, vol. 18, Jul. 22, 2013, pp. 8618-8665; doi:10.3390/molecules18078618.

Reiner et al., "The inverse electron demand Diels-Aider click reaction in Radiochemistry," J. Labelled Comp. Radiopharm., Apr. 2014, 57(4), pp. 285-290; doi:10.1002/jlcr.3149.

Rossin et al., "In Vivo Chemistry for Pretargeted Tumor Imaging in Live Mice," Angew. Chem. Int. Ed., 2010, vol. 49, pp. 3375-3378; DOI: 10.1002/anie.200906294.

Rossin et al., "Supporting Information for In Vivo Chemistry for Pretargeted Tumor Imagining in Live Mice," 2010, Sections S1-S6, pp. S2-S21.

Royzen et al., "A Photochemical Synthesis of Functionalized trans-Cyclooctenes Driven by Metal Composition," J. Am. Chem. Soc., 2008, vol. 130, pp. 3760-3761.

Seif-Naraghi et al., "Safety and Efficacy of an Injectable Extracellular Matrix Hydrogel for Treating Myocardial Infarction," Science Translation Medicine, Feb. 20, 2013, vol. 5, Issue 173, 10 pages.

Selvaraj et al., "Tetrazine-tans-cyclooctene ligation for the rapid construction of integrin $\alpha_v\beta_3$ targeted PET tracer based on a cyclic RGD peptide," Bioorg. Med. Chem. Lett., Sep. 1, 2011; 21(17), pp. 5011-5014; doi:10.1016/j.bmcl.2011.04.116.

(56) References Cited

OTHER PUBLICATIONS

Selvaraj et al., "trans-Cyclooctene—a stable, voracious dienophile for bioorthogonal labeling", Current Opinion in Chemical Biology, vol. 17, Issue 5, Oct. 2013, pp. 753-760; doi:10.1016/j.cbpa.2013.07.031.
Shelke et al., "Polysaccharide biomaterials for drug delivery and regenerative engineering," Polym. Adv. Technol., 2014, vol. 25, pp. 448-460; DOI: 10.1002/pat.3266.
Thalhammer et al., Reaktivitat Einfacher Offenkettiger Und Cyclischer Dienophile Bei Diels-Alder-Reaktionen Mit Inversem Elektronenbedarf, Tetrahedron Letters, 1991, vol. 31, No. 47, pp. 6851-6854.
Versteegen et al., Click to Release: Instantaneous Doxorubicin Elimination upon Tetrazine Ligation, Angew. Chem. Int. Ed., 2013, vol. 52, pp. 14112-14116.
Zeglis et al. "Modular Strategy for the Construction of Radiometalated Antibodies for Positron Emission Tomography Based on Inverse Electron Demand Diels-Alder Click Chemistry," Bioconjugate Chemistry, Aug. 31, 2011, vol. 22, pp. 2048-2059.
Zeglis et al., "A Pretargeted PET Imaging Strategy Based on Bioorthogonal Diels-Alder Click Chemistry," J. Nucl. Med., Aug. 2013, 54(8), pp. 1389-1396; doi: 10.2967/jnumed.112.115840.
Zeglis et al., "Building Blocks for the Construction of Bioorthogonally Reactive Peptides via Solid-Phase Peptide Synthesis," Chemistry Open Communications, 2014, vol. 3, pp. 48-53, DOI: 10.1002/open.201402000.
Zhang et al., "An ionically crosslinked hydrogel containing vancomycin coating on a porous scaffold for drug delivery and cell culture," International Journal of Pharmaceuticals, Nov. 21, 2007, vol. 353, No. 1-2, pp. 74-87.
Alge, D.L. et al. (Apr. 8, 2013, e-published Mar. 8, 2013). "Synthetically tractable click hydrogels for three-dimensional cell culture formed using tetrazine-norbornene chemistry," *Biomacromolecules* 14(4):949-953.
Cok, A.M. et al. (2013). "Synthesis of Model Network Hydrogels via Tetrazine-Olefin Inverse Electron Demand Diels-Alder Cycloaddition," *Macromol Symp* 329:108-112.
Extended European Search Report dated Aug. 10, 2017, for EP Application No. 15761367.0, filed Mar. 16, 2015, 13 pages.
Godoy, C.A. et al. (2010). "Enhanced activity of an immobilized lipase promoted by site-directed chemical modification with polymers," *Process Biochemistry* 45(4):534-541.
Hashida, M. et al. (1977). "Timed-Release of Mitomycin C from Its Agarose Bead Conjugate," *Chem Pharm Bull* 25:2456-2458.
Kojima, T. et al. (Jun. 1978). "Antitumor activity of timed-release derivative of mitomycin C, agarose bead conjugate," *Chem Pharm Bull* 26(6):1818-1824.
Korpela, T. et al. (Mar. 1976). A simple method to introduce aldehydic function to agarose, *Anal Biochem* 71(1):322-323.
Sluyterman, L.A. AE et al. (1981). "Chromatofocusing," Journal of Chromatography 206(3):441-447.
Thomas, T.P. et al. (Sep. 4, 2012, e-published Aug. 7, 2012). "Polyvalent dendrimer-methotrexate as a folate receptor-targeted cancer therapeutic," *Mol Pharm* 9(9):2669-2676.
Tritton, T.R. et al. (Jul. 16, 1982). "The anticancer agent adriamycin can be actively cytotoxic without entering cells," *Science* 217(4556):248-250.

* cited by examiner

Figure 1A
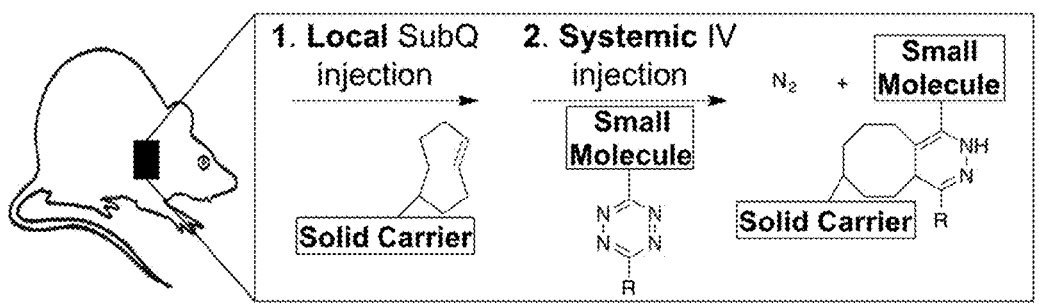
Figure 1B
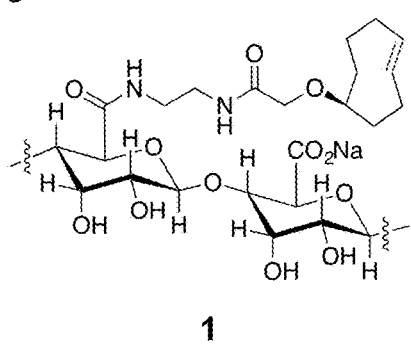
1
trans-cyclooctene modified gel
(TCO-Gel 1)
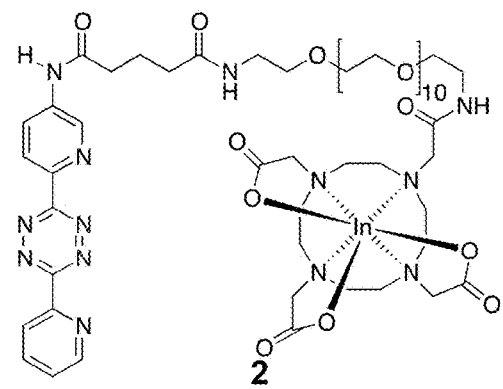
2
Tetrazine-indium-111
($^{111}$In-Tz 2)

Figure 18
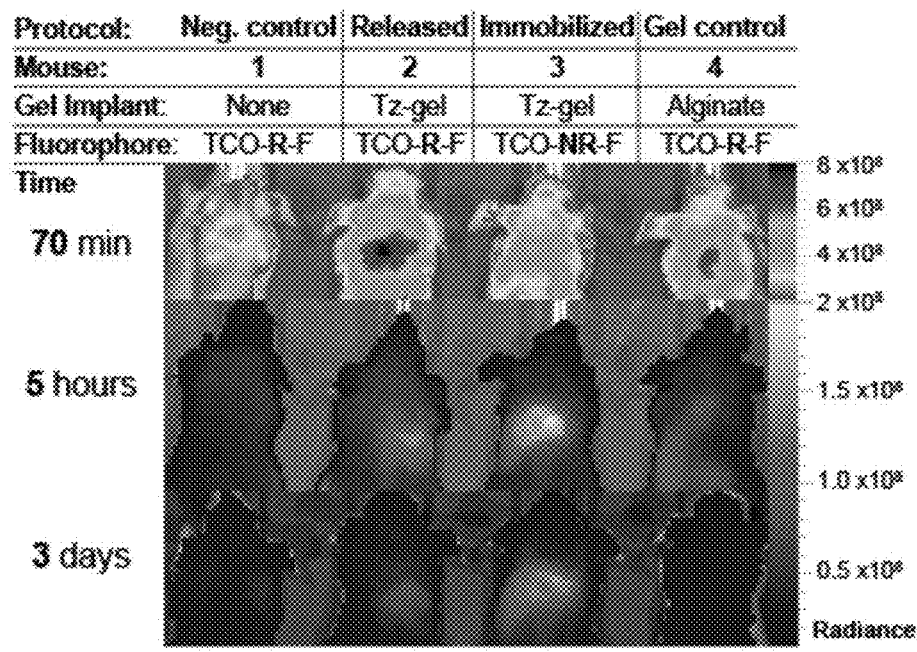
Figure 19A
Figure 19B
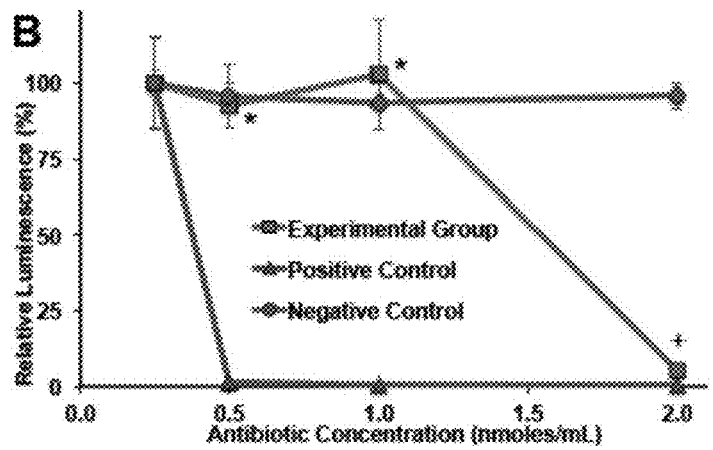

Figure 26     Sample 9(+)

TCO CONJUGATES AND METHODS FOR DELIVERY OF THERAPEUTIC AGENTS

CROSS-REFERENCES TO RELATED APPLICATIONS

This application is a continuation of U.S. application Ser. No. 15/265,158, filed Sep. 14, 2016, which is a continuation of PCT Application No. PCT/US2015/020718, filed Mar. 16, 2015, which claims priority to U.S. Provisional Application Nos. 62/083,022, filed Nov. 11, 2014, 62/013,994, filed Jun. 18, 2014, and 61/953,294, filed Mar. 14, 2014, each of which is incorporated in its entirety herein for all purposes.

STATEMENT AS TO RIGHTS TO INVENTIONS MADE UNDER FEDERALLY SPONSORED RESEARCH AND DEVELOPMENT

Not Applicable

BRIEF SUMMARY OF THE INVENTION

In a first embodiment, the present invention provides a solid support composition having a biocompatible solid support, at least one binding, and a linker having from about 1 to about 10 linking atoms, covalently linking each binding agent to the biocompatible solid support.

In another embodiment, the present invention provides a bioactive composition having a therapeutic or diagnostic agent, a binding agent that can be trans-cyclooctene or tetrazine, and a linker having from about 1 to about 10 linking atoms, covalently linking the binding agent to the therapeutic or diagnostic agent.

In another embodiment, the present invention provides a composition of

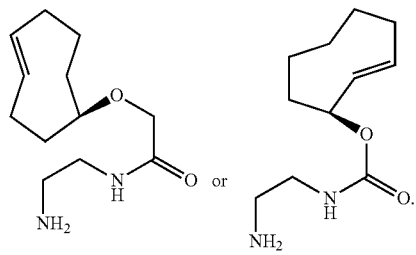

In another embodiment, the present invention provides a method for selectively delivering an effective amount of a therapeutic or diagnostic agent to a first location of a targeted organ or tissue in a patient. The method includes implanting a solid support composition of the present invention in the patient at the first location of the targeted organ or tissue, wherein the solid support composition includes a first binding agent. The method also include administering to the patient a bioactive composition of the present invention, wherein the bioactive composition includes a second binding agent, and wherein the first and second binding agents bind to one another upon contact, thereby selectively delivering the effective amount of the therapeutic or diagnostic agent to the first location of the targeted organ or tissue in the patient.

In another embodiment, the present invention provides a method for selectively delivering an effective amount of a therapeutic or diagnostic agent to a first location of a targeted organ or tissue in a patient. The method includes implanting in the patient at the first location of the targeted organ or tissue a solid support composition having a biocompatible solid support and a first binding agent linked to the solid support. The method also includes administering to the patient a bioactive composition having a therapeutic or diagnostic agent, a second binding agent complementary to the first binding agent, and a releasable linker linking the therapeutic or diagnostic agent and the second binding agent, such that the first and second binding agent bind to one another upon contact. The method also includes releasing the therapeutic or diagnostic agent, thereby delivering the therapeutic or diagnostic agent to the first location of the targeted organ or tissue.

BRIEF DESCRIPTION OF THE DRAWINGS

FIG. 1A and FIG. 1B shows the method of the present invention involving the initial injection of a biomaterial covalently attached to TCO. This is followed by a systemic injection of a therapeutic agent coupled to the tetrazine moiety. When the two entities come in close proximity, they react covalently attaching the therapy to the solid carrier and thus localizing the therapeutic agent. A molecular probe was utilized for Tz radioprobe 2 that contains radioactive [111] Indium.

FIG. 18 shows radiance values for mice at 70 minutes, 5 hours and 3 days, without a gel impantation or implanted with Tz-gel, or alginate only, and then injected with TCO-R-rhodamine or TCO-NR-rhodamine.

FIG. 19A and FIG. 19B shows the MIC of TCO-R-vancomycin for luminescent MSSA (Xen 29).

DETAILED DESCRIPTION

I. General

Figure 2:
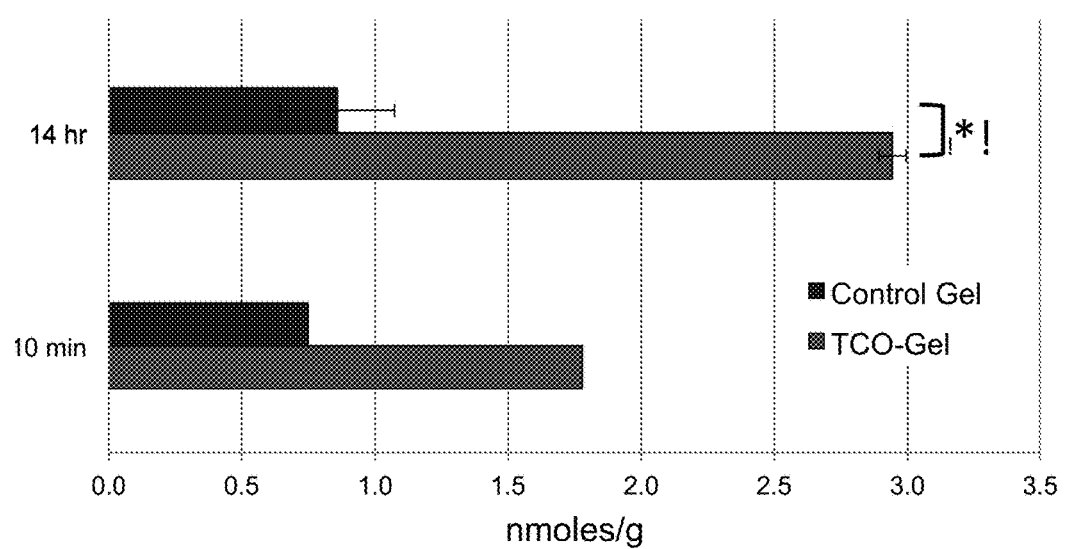
FIG. 2 shows in-vitro studies, pre-weighed gel discs (experimental or control) were mixed with a solution of Tz radioprobe 2 for 10 min or 14 hours. During a 10 minute exposure a sample of TCO-Gel 1 bonded 1.78 nmoles/g, while the control gel maintained 0.75 nmoles/g of Tz radioprobe 2. In 14 hours the amount of Tz-radioprobe attached to control gel remained constant at 0.86 nmoles/g. The TCO-Gel 1 bound 2.78 nmoles/g. Error bars represent the standard deviation of the mean for three replicates. Star indicates statistical significance by paired t-test (p-value<0.05).
Figure 3A:
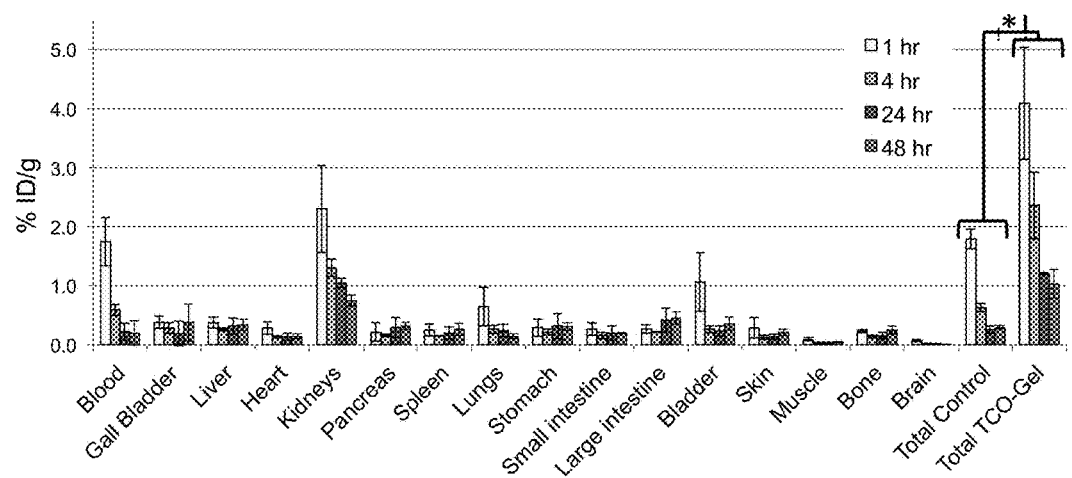
FIG. 3A and FIG. 3B shows Biodistribution results of Tz radioprobe 2 a, Mice (n=3) bearing subcutaneous TCO-Gel 1 (mean 0.23 g [0.10-0.29 g]) and control gel (Mean 0.23 g [0.16-0.25 g]) were administered Tz radioprobe 2 (mean 44 µCi [39.2-48.4 µCi]) via tail vein injection (t=0). b, Mean difference at specific timepoints between TCO-Gel 1 & control gel. Bars indicate % ID/g per organ at specific timepoint (1, 4, 24, 48 hr). Error bars represent the standard deviation of the mean for three replicates. Star indicates statistical significance by paired t-test (p-value<0.05).
Figure 3B:
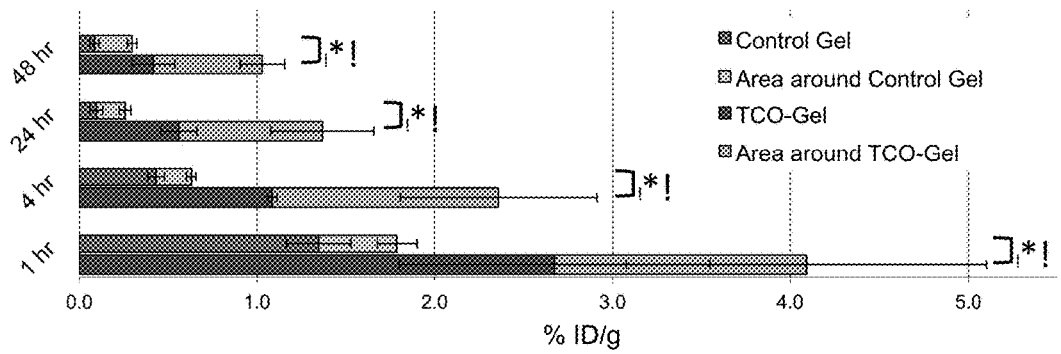
Figure 4:
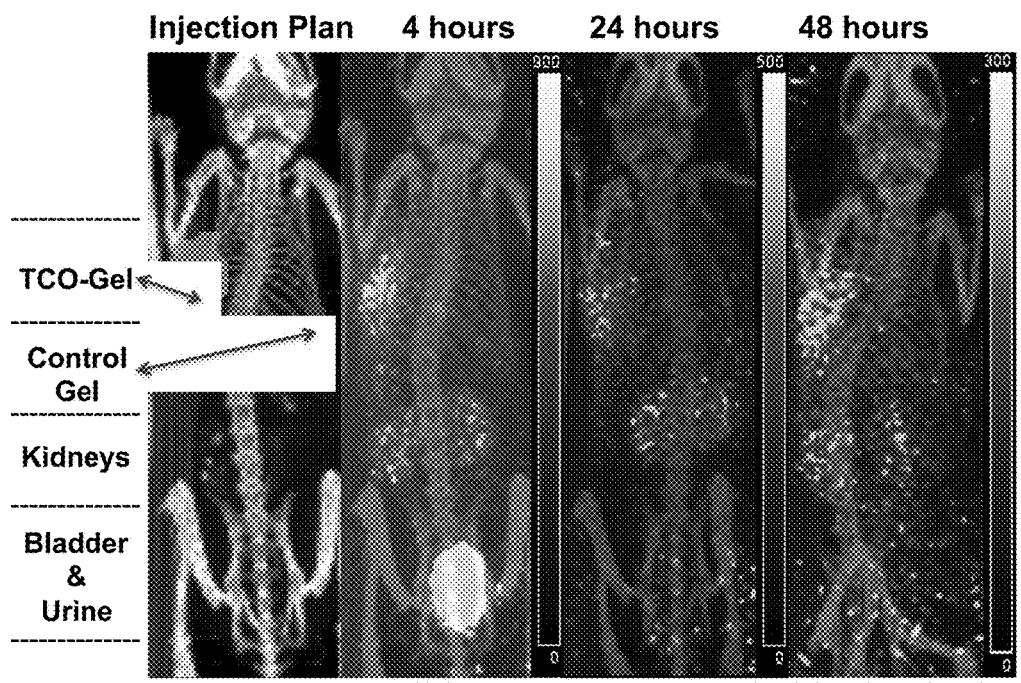
FIG. 4 shows a mouse bearing subcutaneous TCO-Gel 1 (170 mg, green area) and control gel (230 mg, yellow area). 3 hours after implantation Tz radioprobe 2 (1.05 mCi) was delivered via tail vein injection and imaged at 4, 24, 48 hour through SPECT.
Figure 5:
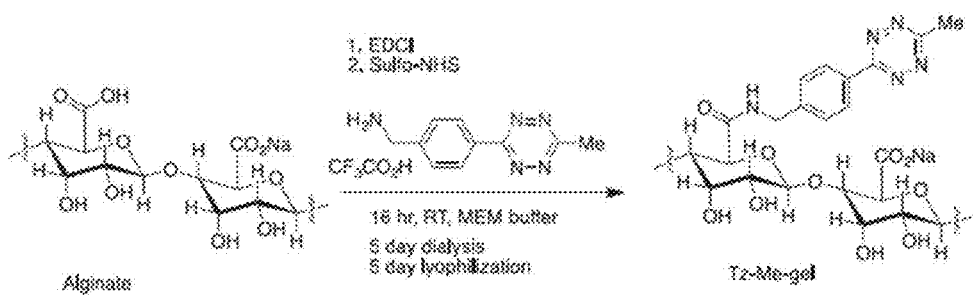
FIG. 5 shows synthetic preparation of the solid support composition Tz-Me-gel.
Figure 6:
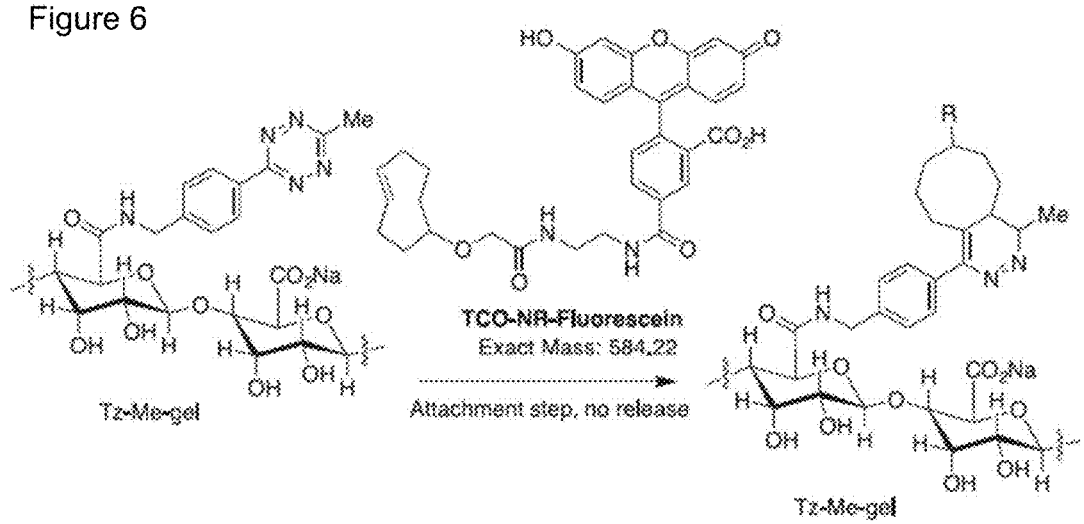
FIG. 6 shows the reaction between the tetrazine solid support and fluorescein linked with TCO through a non-releasable linker. R represents the intact diethyl amine fluorescein moiety, still covalently connected to the solid support.
Figure 7:
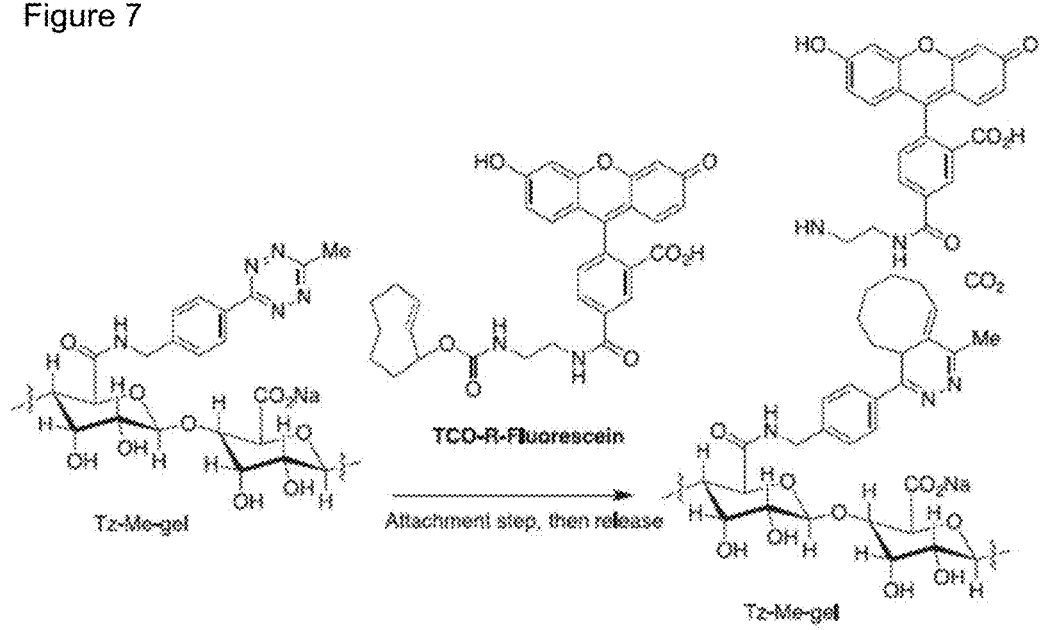
FIG. 7 shows the reaction between the tetrazine solid support and fluorescein linked with TCO through a releasable linker. As expected fluorescein diethyl amine (MW: 418.40) and carbon dioxide are released from the solid support.
Figure 8:
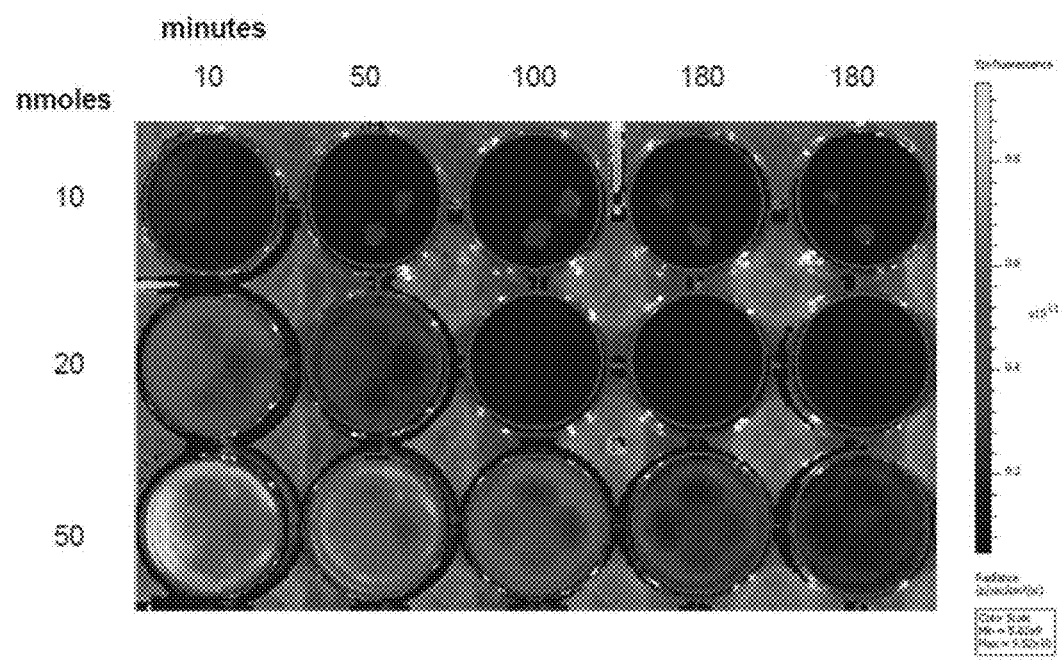
FIG. 8 provides a sample of the supernatants after removal of the gel used to extrapolate the amount of unreacted TCO-X-Fluorescein and the kinetics of the reaction between TCO-X-Fluorescein and Tz-Me-gel. Briefly, the method involved: forming and weighing the Tz-gel, adding 1 mL of PBS saline containing a predetermined concentration of TCO-X-Fluorescein (10, 20, 50 nmoles), placing the plate at a well-plate mixer (speed 200) for predetermined number of time (10, 50, 100, 180 minutes), transferring the supernatant at the specific timepoint to another plate, and measuring the amount of fluorescence remaining in the supernatant via an IVIS spectrum machine (Fluorescein excitation at 490 nm, emission at 515 nm).
Figure 9:
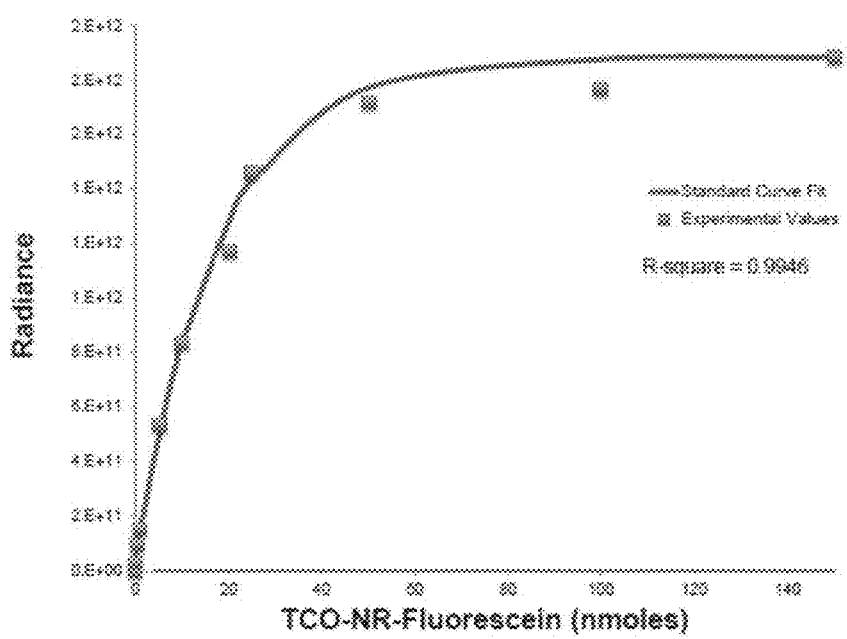
FIG. 9 shows a standard curve fit correlating radiance (fluorescence) and amount of fluorophore based on experimental values with a known amount of nmoles of TCO-NR-Fluorescein and the radiance detected with an IVIS Spectrum machine (Fluorescein excitation at 490 nm, emission at 515 nm).
Figure 10:
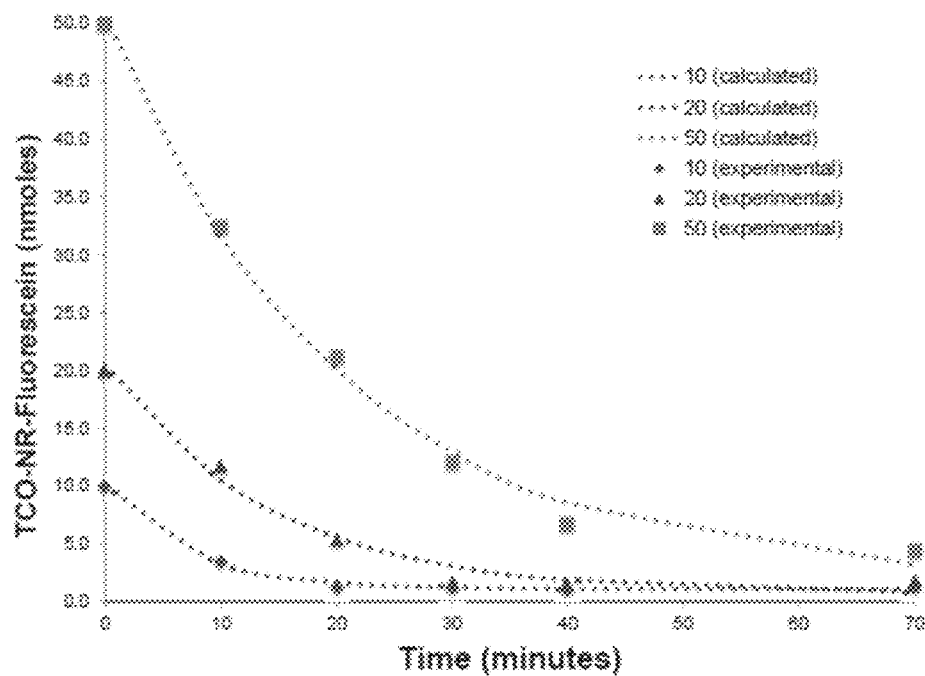
FIG. 10 shows the decrease of TCO-NR-Fluorescein in the supernatant over time when the TCO-NR-Fluorescein and Tz-Me-gel are mixed at 37° C. between 0 and 70 minutes.
Figure 11:
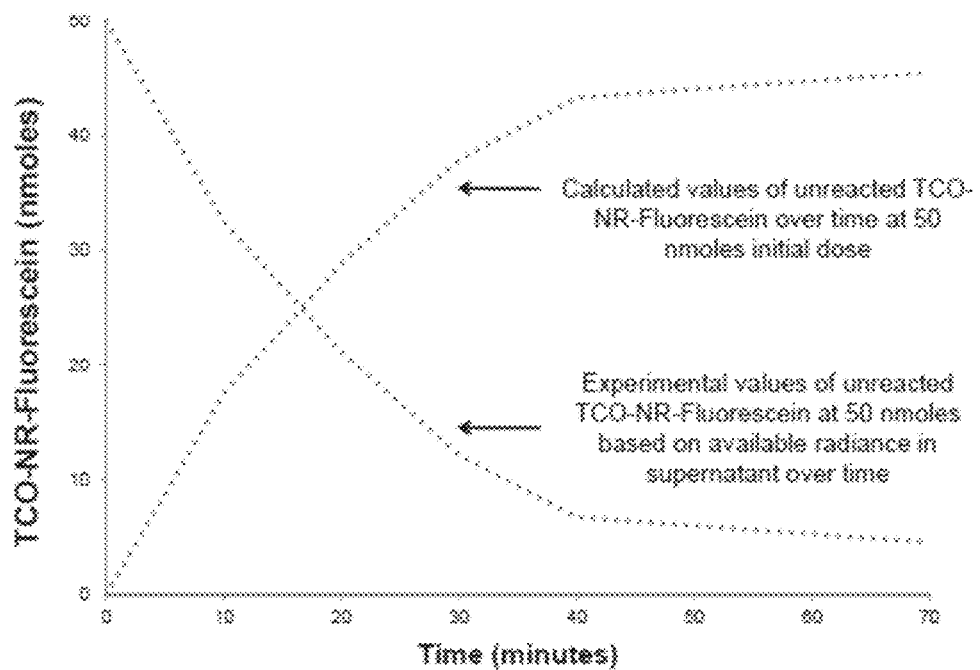
FIG. 11 shows the theoretical reciprocity of TCO-NR-Fluorescein bound to the gel and the amount detected in the supernatant that remains unbound.
Figure 12:
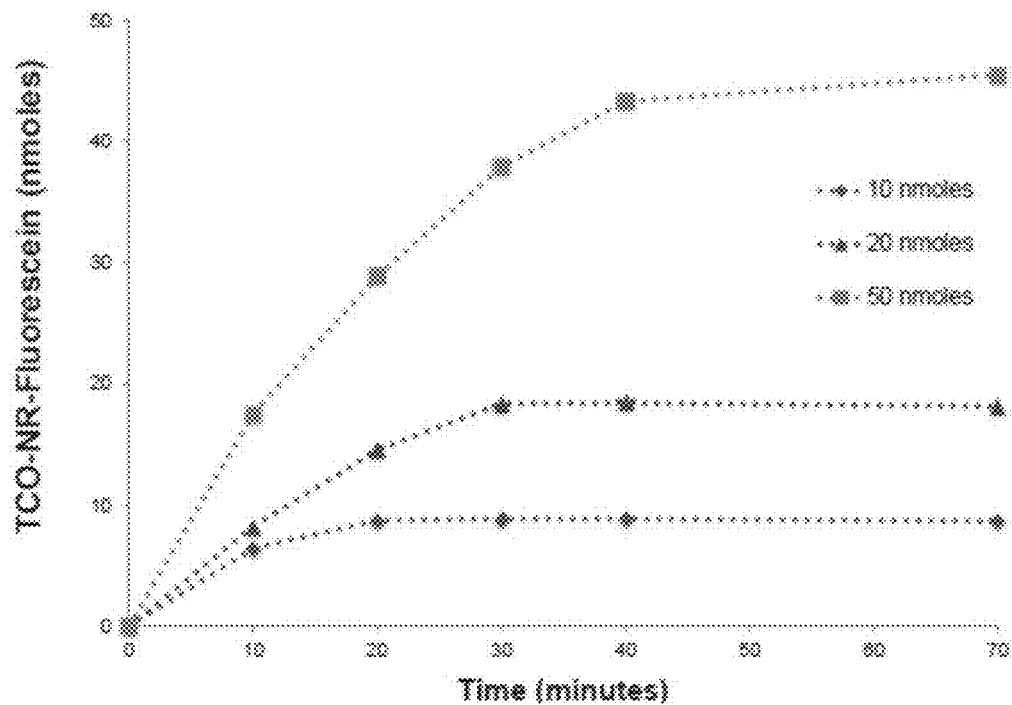
FIG. 12 shows the calculated amount of bound TCO-NR-Fluorescein molecules to Tz-Me-gel based on the data of FIG. 10. Based on the data presented when a Tz-Me-gel disc was mixed with 50 nmoles of TCO-NR-Flourescein, 0.66 nmoles of TCO-NR-Fluorescein reacted per 1 mg of Tz-Me-gel after 70 minutes (0.66 nmoles/mg). Even after only 70 minutes this is about 200 times higher that the amount achieved with TCO-gel (2.78 nmoles/g) after 14 hours as shown in FIG. 2.
Figure 13:
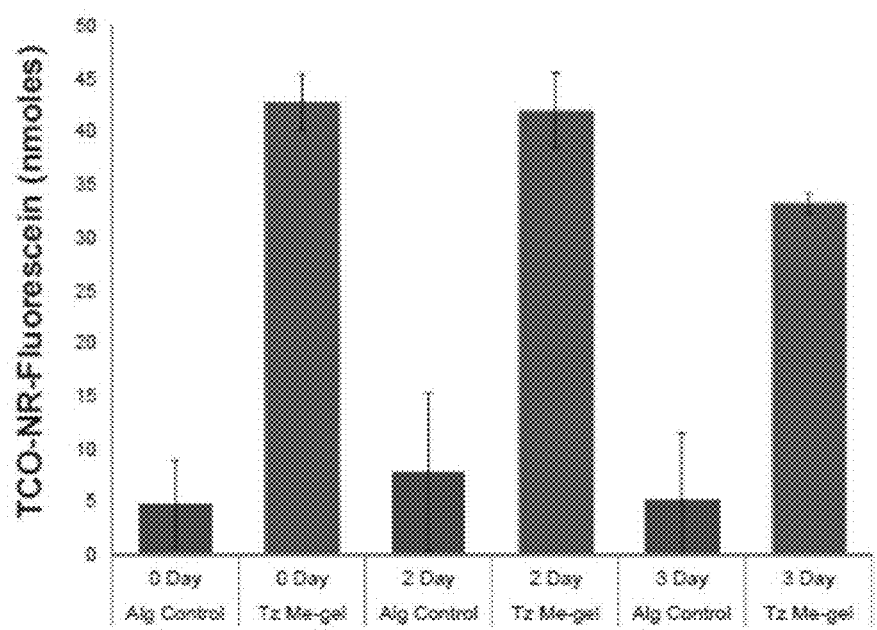
FIG. 13 shows the activity of Tz-Me-gel after incubation at 37° C. for a predetermined amount of time (0-3 days). After the allotted incubation, 50 mg gels were challenged with the addition of 50 nmoles of TCO-NR-Fluorescein for 90 minutes and the amount bound was calculated as in the previous figures.
Figure 14:
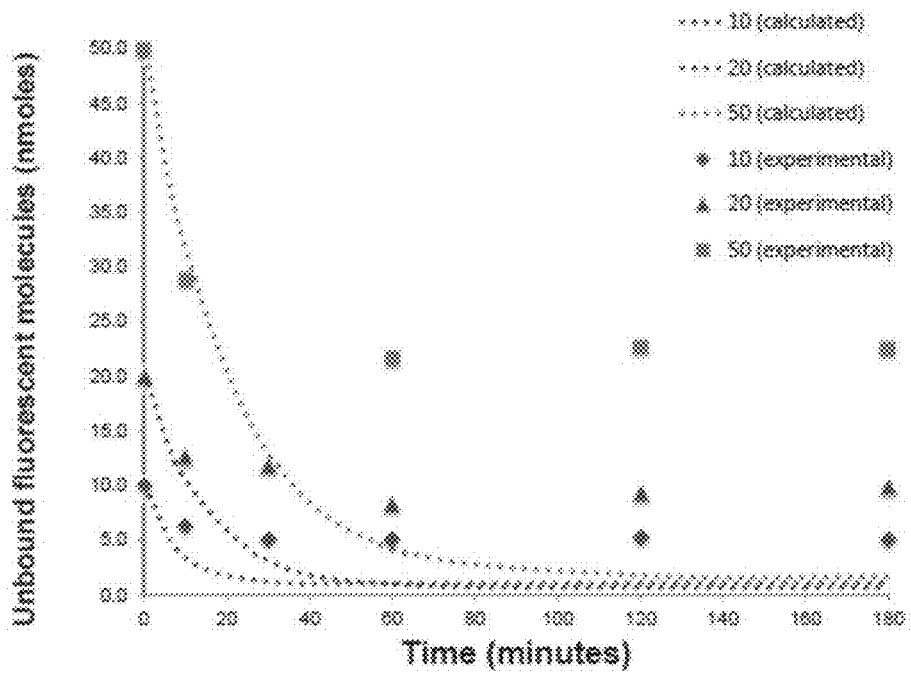
FIG. 14 shows the expected versus observed amount of unbound molecules after addition of TCO-R-fluorescein to Tz-Me-gel after multiple time-points. Given the similarities between the TCO-R-Fluorescein and TCO-NR-Fluorescein, similar reactivity patterns are expected. The assumption is that the difference in amount of recovered fluorescence in the supernatant is due to the release of diethylfluorescein as illustrated in FIG. 7.
Figure 15:
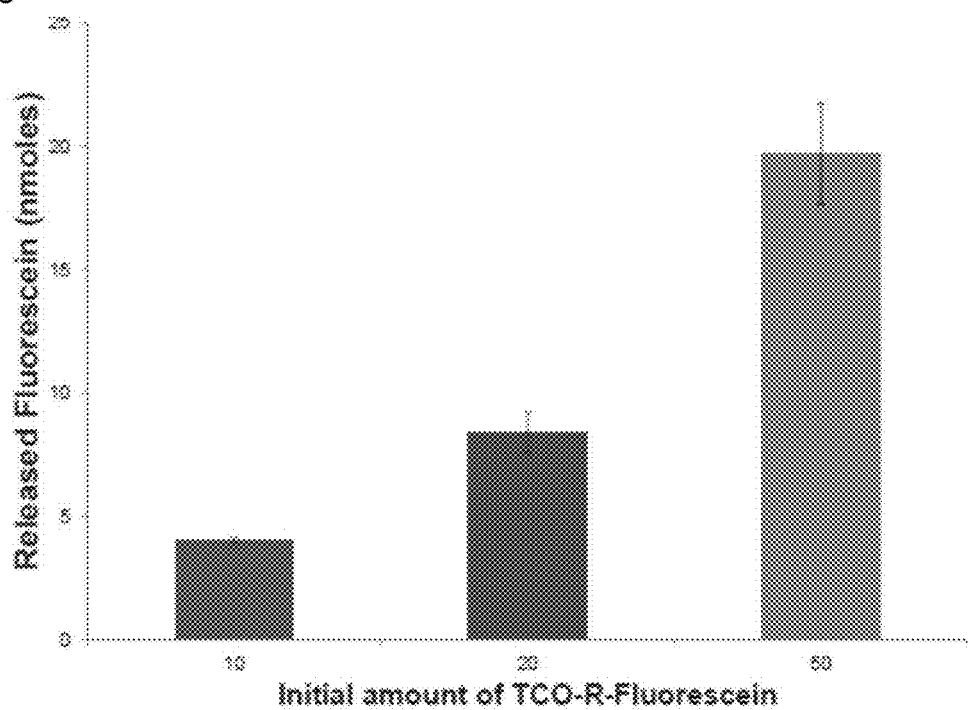
FIG. 15 shows the total amount of fluorescein released after the addition of a specific amount of TCO-R-fluorescein (10, 20 & 50 nmoles) to Tz-Me-gel. Furthermore, the specific identity of the compounds in the supernatant of time point 60 minutes were analyzed with an LC-MS and revealed the presence of Fluorescein diamine (MW 418.40) as the main compound, further confirming the presence of the elimination product of the Catch & Release reaction of TCO-R-Fluorescein with Tz-Me-gel.

The present invention provides compositions for implanting and administering to a subject where the compositions use a short linker that can also include a releasable component. The releasable linker allows administration of a greater amount of therapeutic or diagnostic agent to the patient in need thereof.

II. Definitions

"Therapeutic agent" refers to an agent capable of treating and/or ameliorating a condition or disease. Representative therapeutic agents include, but are not limited to, paclitaxel, doxorubicin, etoposide, irinotecan, SN-38, cyclosporin A, podophyllotoxin, Carmustine, Amphotericin, Ixabepilone, Patupilone (epothelone class), vancomycin, rapamycin and platinum drugs. The therapeutic agent of the present invention also include prodrug forms.

"Diagnostic agent" refers to agents that assist in diagnosing conditions or diseases. Representative diagnostic agents including imaging agents such as paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to, $^3$H, $_{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

"Targeted organ or tissue" refers to an organ or tissue that is being targeted for delivery of the therapeutic or diagnostic agent. Representative organs and tissues for targeting include those that can be targeted by chemical or biological targeting agents, as well as those organs and tissues that cannot be targeted by chemical or biological targeting agents. Representative organs or tissues include bone.

"Selectively delivering" refers to delivering a therapeutic or diagnostic agent to a portion of an organ or tissue in need of treatment, without targeting other portions of the organ or tissue not in need of treatment.

"Implanting " refers to surgical implantation into the patient's body.

"Biocompatible solid support" refers a solid support material capable of implantation into the patient's body and supporting one of the binding agents, as well as the therapeutic or diagnostic agent after the binding agents conjugate. The solid support is compatible with the patient's body. Representative biocompatible solid supports include, but are not limited to, hydrogels such as polysaccharide hydrogels, alginate, cellulose, chitosan, hyaluronic acid, chondroitin sulfate, heparin, and others.

"Contacting" or "contact" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Linker", "linked" or "linking" refers to a chemical moiety that links the compound of the present invention to a biological material that targets a specific type of cell, such as a cancer cell, other type of diseased cell, or a normal cell type. The linking can be via covalent or ionic bond formation. The linking can be direct linkage between to the two moieties being linked, or indirectly, such as via a linker. Linkers useful in the present invention can be up to 30 carbon atoms in length. Preferably, the linkers are 5-15 carbon atoms in length. The types of bonds used to link the linker to the compound and biological molecule of the present invention include, but are not limited to, amides, amines, esters, carbamates, ureas, thioethers, thiocarbamates, thiocarbonate and thioureas. One of skill in the art will appreciate that other types of bonds are useful in the present invention.

"Binding agent" refers to any group capable of forming a covalent bond to another binding agent in a biological environment. This is often referred to as bioconjugation or bioorthogonal chemistry. Representative binding agents include, but are not limited to, an amine and an activated ester, an amine and an isocyanate, an amine and an isothiocyanate, thiols for formation of disulfides, an aldehyde and amine for enamine formation, an azide for formation of an amide via a Staudinger ligation, an azide and alkyne for formation of a triazole via Click-chemistry, trans-cyclooctene (TCO) and tetrazine, and others. The binding agents useful in the present invention have a high reactivity with the corresponding binding agent so that the reaction is rapid.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Patient" refers to animals in need of treatment, such as mammals, including, but not limited to, primates (e.g., humans), cows, sheep, goats, horses, dogs, cats, rabbits, rats, mice and the like. In certain embodiments, the patient is a human.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Cal-* culations (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

III. Compositions

The present invention provides compositions having a short linker or a releasable linker for selectively delivering a therapeutic or diagnostic agent to a patient. In some embodiments, the present invention provides a solid support composition having a biocompatible solid support, at least one binding agent, and a linker having from about 1 to about 10 linking atoms, covalently linking each binding agent to the biocompatible solid support.

Any suitable biocompatible solid support can be used in the method of the present invention. For example, the biocompatible solid support can be a hydrogel, a cross-linked polymer matrix, a metal, a ceramic, a plastic, among others. Hydrogels useful in the present invention include, but are not limited to, polysaccharide hydrogels, alginate, cellulose, hyaluronic acid, chitosan, chitosin, chitin, hyaluronic acid, chondroitin sulfate, heparin, and others. Other sugar-based biomaterials are known in the art, such as those described in Polymer Advanced Technology 2014, 25, 448-460. Polymers useful as the biocompatible support can include, but are not limited to, polyphosphazenes, polyanhydrides, polyacetals, poly(ortho esters), polyphosphoesters, polycaprolactones, polyurethanes, polylactides, polycarbonates, polyamides, and polyethers, and blends/composites/co-polymers thereof Representative polyethers include, but are not limited to, Poly(ethylene glycol) (PEG), poly(propylene glycol) (PPG), triblock Pluronic ([PEG]n-[PPG]m-[PEG]n), PEG diacrylate (PEGDA) and PEG dimethacrylate (PEGDMA). The biocompatible solid support can also include proteins and other poly(amino acids) such as collagen, gelatin, elastin and elastin-like polypeptides, albumin, fibrin, poly(gamma-glutamic acid), poly(L-lysine), poly(L-glutamic acid), and poly(aspartic acid).

In some embodiments, the solid support can be a hydrogel. In some embodiments, the solid support can be alginate. In some embodiments, the solid support can be chitin. In some embodiments, the solid support can be hyaluronic acid. In some embodiments, the solid support can be chitosin. In some embodiments, the solid support can be agarose.

Any suitable linker can be used in the present invention to link the binding agent to the biocompatible solid support or the therapeutic or diagnostic agent. Representative linkers can have about 1 to about 100 linking atoms, and can include ethylene-oxy moieties, amines, esters, amides, ketone, urea, carbamate and carbonate functional groups. Other linkers useful in the methods of the present invention can have from about 1 to about 50 linking atoms, or from about 1 to about 10 linking atoms, or from about 5 to about 10 linking atoms. Representative linkers include, but are not limited to, those shown below:

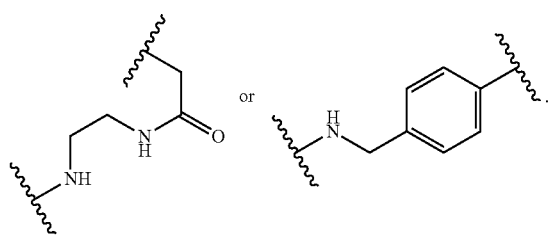 [SMILES: *CC(=O)NCCN* ; *NCc1ccc(*)cc1]

Other linkers suitable in the present invention include:

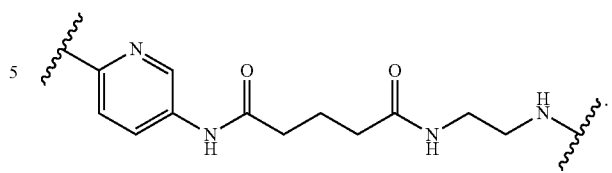

Any suitable binding agent can be used in the method of the present invention. Representative binding agents can be found in "Bioconjugate Techniques" Greg T. Hermanson, 1996 and *ACS Chemical Biology* 2014, 9, 592-605. For example, binding agents useful in the method of the present invention include, but are not limited to, cyclooctene, tetrazine, azide, alkyne, amine, activated ester, isocyanate, isothiocyanate, thiol, aldehyde, amide, and others. In some embodiments, the binding agent can be cyclooctene, tetrazine, azide or alkyne. In some embodiments, the binding agent can be trans-cyclooctene or 1,2,4,5-tetrazine. In some embodiments, the binding agent can be trans-cyclooctene. In some embodiments, the binding agent can be 4-methyl-1,2,4,5-tetrazine.

In some embodiments, the binding agent and the linker together have the structure of:

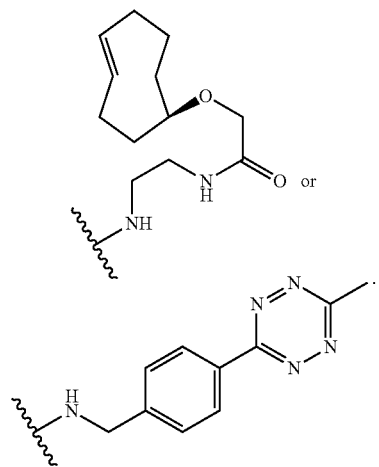

In some embodiments, the composition can have the structure of:

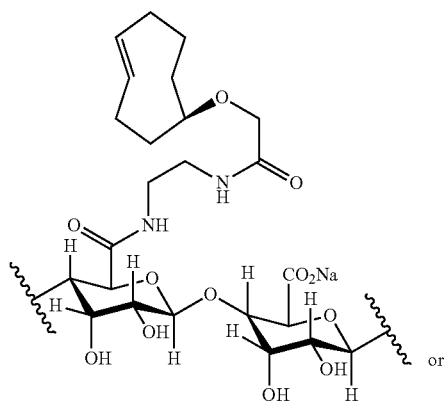

-continued

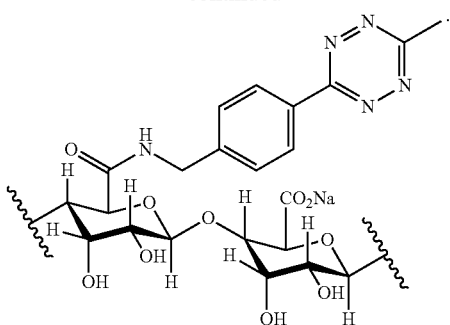

The present invention also provides compositions of a therapeutic agent or diagnostic agent linked to a binding agent via a linker. In some embodiments, the present invention provides a bioactive composition having a therapeutic or diagnostic agent, a binding agent that can be trans-cyclooctene or tetrazine, and a linker having from about 1 to about 10 linking atoms, covalently linking the binding agent to the therapeutic or diagnostic agent.

Any therapeutic or diagnostic agent can be used in the method of the present invention. Representative therapeutic agents include, but are not limited to, antibiotics such as vancomycin, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. Other therapeutic agents include doxycyclin and other MMP inhibitors. Still other therapeutic agents include daptomycin, L-dopa, oseltamivir, cefalexin, 5-aminolevulinic acid, cysteine, nystatin, amphotericin B, flucytosine, emtricitabine, trimethoprim, sulfamethoxazole, acyclovir, celecoxib, nimodipine, doxycycline, ceftriazone, among others. In some embodiments, the therapeutic agent can be vancomycin. In other embodiments, the therapeutic agent can be daptomycin. In yet other embodiment the therapeutic agent can be doxorubicin. In another embodiment, the therapeutic agent can be cyclic-adenosine monophosphatidyl (c-AMP).

Representative diagnostic agents including imaging agents such as paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to, $^3$H, $_{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $_{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am. The diagnostic agents can also include chelators such as 1,4,8,11-tetraazacyclododecane-1,4,8,11-tetraacetic acid (TETA), 4,11-bis(carboxymethyl)-1,4,8,11-tetraazabicyclo[6.6.2]hexadecane (CB-TE2A), diethylenetriaminepentaacetice acid (DTPA) and 1,4,7,10-tetra-azacyclodecanetetraacetic acid (DOTA). Other chelators are useful in the method of the present invention.

Any suitable linker can be used in the present invention to link the binding agent to the biocompatible solid support or the therapeutic or diagnostic agent. Representative linkers can have about 5 to about 100 linking atoms, and can include ethylene-oxy moieties, amines, esters, amides, ketone, urea, carbamate and carbonate functional groups. Other linkers useful in the methods of the present invention can have from about 5 to about 50 linking atoms, or from about 1 to about 10 linking atoms, or from about 5 to about 10 linking atoms. Representative linkers include, but are not limited to, those shown below:

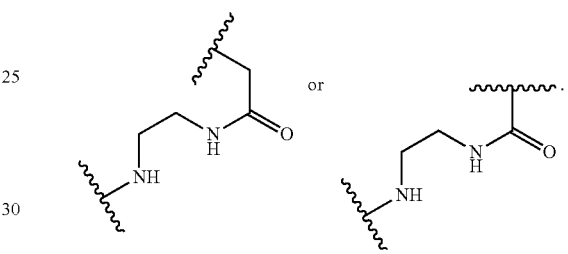

Any suitable binding agent can be used in the method of the present invention. Representative binding agents can be found in "Bioconjugate Techniques" Greg T. Hermanson, 1996 and ACS Chemical Biology 2014, 9, 592-605. For example, binding agents useful in the method of the present invention include, but are not limited to, cyclooctene, tetrazine, azide, alkyne, amine, activated ester, isocyanate, isothiocyanate, thiol, aldehyde, amide, and others. In some embodiments, the binding agent can be cyclooctene, tetrazine, azide or alkyne. In some embodiments, the binding agent can be trans-cyclooctene or 1,2,4,5-tetrazine. In some embodiments, the binding agent can be trans-cyclooctene. In some embodiments, the binding agent can be 4-methyl-1,2,4,5-tetrazine.

In some embodiments, the binding agent and the linker together have the structure of:

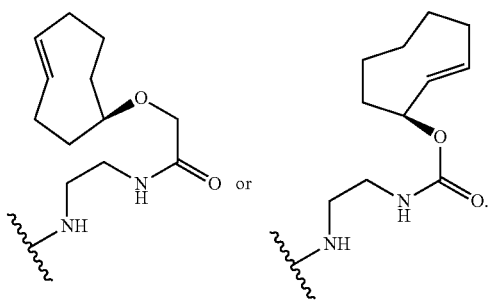

In some embodiments, the present invention provides a composition of

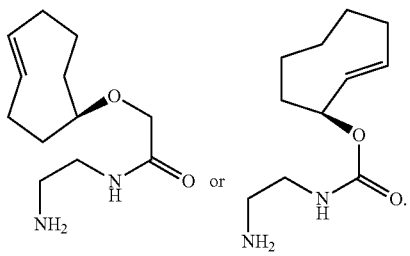

IV. Method For Selectively Delivering Therapeutic Or Diagnostic Agent

The present invention provides a method for selectively delivering a therapeutic or diagnostic agent by implanting the solid support composition of the present invention in a patient in need thereof, followed by administering to the patient the bioactive composition of the present invention. In some embodiments, the present invention provides a method for selectively delivering an effective amount of a therapeutic or diagnostic agent to a first location of a targeted organ or tissue in a patient. The method includes implanting a solid support composition of the present invention in the patient at the first location of the targeted organ or tissue, wherein the solid support composition includes a first binding agent. The method also include administering to the patient a bioactive composition of the present invention, wherein the bioactive composition includes a second binding agent, and wherein the first and second binding agents bind to one another upon contact, thereby selectively delivering the effective amount of the therapeutic or diagnostic agent to the first location of the targeted organ or tissue in the patient.

Any suitable organ or tissue can be targeted using the method of the present invention. Representative organs or tissues include, but are not limited to, bone, cartilage, ligaments, tendons, intestines, muscles, nervous system including brain, spinal cord, heart, and nerves, and others. For example, when the organ is the heart, the method of the present invention can be used for cardiac repair. In some embodiments, the first location of the targeted organ or tissue cannot be selectively targeted by chemical or biological targeting agents over other locations of the targeted organ or tissue in the patient. In some embodiments, the targeted organ or tissue can be bone.

Binding agents suitable in the method of the present invention are described in more detail above for the solid support composition and the bioactive composition. In some embodiments, the first binding agent can be trans-cyclooctene and the second binding agent can be tetrazine. In some embodiments, the second binding agent can be 1,2,4,5-tetrazine. In some embodiments, the second binding agent can be 4-methyl-1,2,4,5-tetrazine.

In some embodiments, the implantable composition can have the structure:

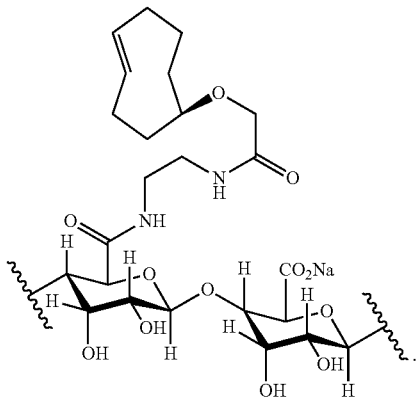

In some embodiments, the implantable composition can be:

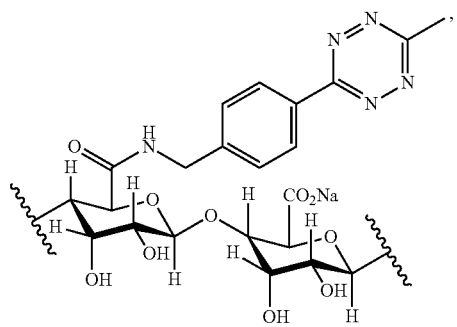

and the bioactive composition can be:

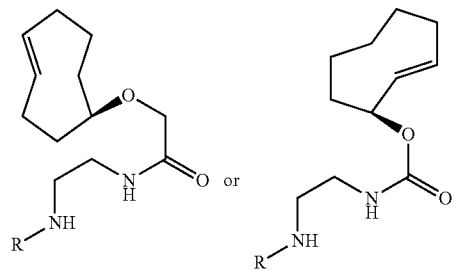

wherein R can be the therapeutic agent or the diagnostic agent.

The biocompatible solid support can be implanted by any means known to one of skill in the art.

The therapeutic or diagnostic agent can be administered in any suitable amount sufficient to treat the disease or condition the patient is suffering from. The dose, frequency and timing of such administering will depend in large part on the selected therapeutic agent, the nature of the condition being treated, the condition of the subject including age, weight and presence of other conditions or disorders, the formulation being administered and the discretion of the attending physician. Generally, the therapeutic or diagnostic agents are administered in dosages ranging from about 2 mg up to about 2,000 mg per day, although variations will necessarily occur depending, as noted above, on the disease target, the patient, and the route of administration. The therapeutic or diagnostic agents of the present invention can be administered as frequently as necessary, including hourly, daily, weekly or monthly.

The therapeutic or diagnostic agents utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, can be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time, but is typically lower than the dose required to treat the patient without having implanted the biocompatible solid support that concentrates the therapeutic or diagnostic agent at the organ or tissue requiring treatment. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage can be divided and administered in portions during the day, if desired. Doses can be given daily, or on alternate days, as determined by the treating physician. Doses can also be given on a regular or continuous basis over longer periods of time (weeks, months or years).

In some embodiments, the concentration of the therapeutic or diagnostic agent at the first location of the targeted organ or tissue is greater than the concentration elsewhere in the patient. In some embodiments, the therapeutic agent is vancomycin.

In another embodiment, the present invention provides a method for selectively delivering an effective amount of a therapeutic or diagnostic agent to a first location of a targeted organ or tissue in a patient. The method includes implanting in the patient at the first location of the targeted organ or tissue a solid support composition having a biocompatible solid support and a first binding agent linked to the solid support. The method also includes administering to the patient a bioactive composition having a therapeutic or diagnostic agent, a second binding agent complementary to the first binding agent, and a releasable linker linking the therapeutic or diagnostic agent and the second binding agent, such that the first and second binding agent bind to one another upon contact. The method also includes releasing the therapeutic or diagnostic agent, thereby delivering the therapeutic or diagnostic agent to the first location of the targeted organ or tissue.

V. Formulation

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the compounds of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

VI. Administration

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

VII. Examples

Materials. All reagents and NMR solvents were purchased from Sigma-Aldrich (St. Louis, Miss.), unless otherwise noted. Compound 2 was obtained from Iris Biotech (Marktredwitz, Germany), while compound 8 was purchased from Polypure (Oslo, Norway). DOTA-NHS ester was obtained from Macrocyclics (Dallas, Tex.). Silica gel was purchased from Silicycle (Quebec, Canada), while preparative TLC plates (20×20 cm; 1000 μm in thickness) were purchased from Analtech (Newark, Del.). Ultrapure alginates were purchased from ProNova Biomedical (Norway). [$^{111}$In] Indium chloride solutions was purchased from PerkinElmer (Waltham, US) [$^{64}$Cu] Copper chloride in dilute HCl was purchased from Washington University (St. Louis, Mo.) or was produced in-house by the 64Ni(p,n)64Cu nuclear reaction using an 11 MeV Siemens RDS 111 cyclotron and purified by anion exchange chromatography (Biorad AG 1-X8). Dulbecco's Phosphate Buffered Saline (DPBS) was purchased from Invitrogen Corporation (Carlsbad, Calif.).

Methods. NMR experiments were carried out in $CDCL_3$ or [$D_6$] DMSO, using a Varian 400 MHz VNMRS machine. High resolution ESI mass spectrometry data was obtained using Agilent Ion Trap LC/MSD SL at Boston University Chemical Instrumentation Center measured either in the positive or negative. During the organic synthesis phase, an Agilent 1100 Series system equipped with a Waters XBridge C18 Column (19×250 mm) applying a gradient of water and MeCN containing 0.1% TFA was used for HPLC purification.

During radiochemistry and for in-vivo analyses and purifcations, reversed-phase HPLC was performed using a Beckman-Colter System Gold 128 (Brea, Calif.) chromatography systems equipped with Jupiter Proteo C-12 columns (250× 4.6 mm, 4 μm, Phenomenex, Torrance, Calif.) and single wavelength or diode array UV detectors (set to 220 & 254 nm) connected in series to a Bioscan FlowCount photomultiplier tube (PMT) (Bioscan, Washington, D.C.). Data was analyzed using the 32 Karat software package Beckman-Colter). Mobile phase consisted of Solvent A: 0.05% trifluoroacetic acid in water and Solvent B: 100% acetonitrile, a flow rate of 1.5 mL/min, and a linear gradient beginning at 2 min after injection from 9% Solvent B then increasing to 81% over a 30 min period unless otherwise stated.

During in-vitro experiments using alginate gel, molecular sieving high performance liquid chromatography (HPLC) was performed on a Waters Breeze chromatography system with a Waters 2487 dual absorbance detector (220 & 320 nm) and a Bioscan Flow-count radioactivity detector. A Phenomenex BioSep SEC-S3000 column (7.8×300 mm) was eluted in isocratic 0.1 M sodium phosphate, pH 6.8, at 1.0 mL/min.

The $^{64}$Cu and $^{111}$In-labeling yields were determined by radio-TLC, using ITLC-SG strips (Pall Life Sciences, Ann Arbor, Mich.) eluted with 200 mM EDTA in 0.9% aq. NaCl and performed using a Bioscan 200 imaging scanner (Bioscan, Washington D.C.). In these conditions, free radionuclides migrate with Rf=0.9, while radionuclides attached to tetrazine 6 remain at the origin.

PET/CT data was acquired using an Inveon Preclinical Imaging Station (Siemens Medical Solutions.

Animal Handling. All animals were handled in accordance with a protocol approved by the University of California, Davis, Animal Use and Care Committee.

Statistical analysis. Group variation is described as the mean±one standard deviation. Single groups were compared with a two-tailed unpaired t test. Groups with P<0.05 were considered significantly different. Microsoft Excel version 12.8.9 was used for all statistical calculations.

Example 1

Preparation of TCO-Modified Alginate 1

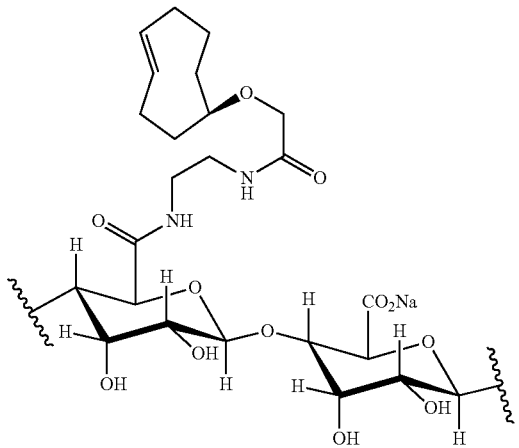

The preparation of TCO-modified alginate is described below, by first preparing the TCO-linker, and coupling to the alginate.

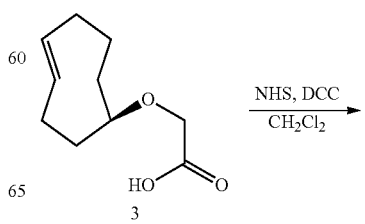

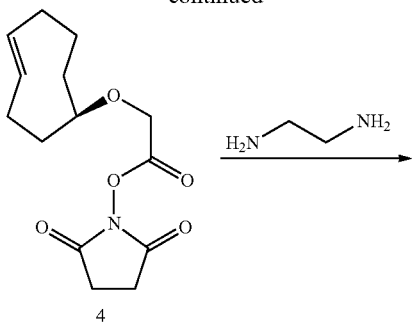

4

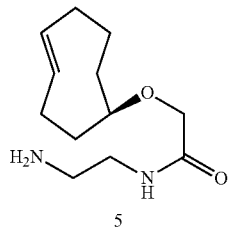

5

(R,E)-N-(2-aminoethyl)-2-(cyclooct-4-en-1-yloxy)acetamide (5). Compound 3 (100 mg, 0.54 mmol), N-hydroxysuccinamide (69 mg, 0.60 mmol) and N,N'-dicyclohexylcarbodiimide (123 mg, 0.60 mmol) was dissolved in $CH_2Cl_2$ (2 mL) and stirred at rt for 2 h. The precipitated urea was filtered off through PVDF membrane. The membrane was washed with $CH_2Cl_2$ (1 mL). The mother liquer was added to a stirring solution of ethylenediamine (324 mg, 5.4 mmol) in $CH_2Cl_2$ (10 mL). The reaction was stirred at rt for 2 h. The reaction mixture was washed with water (2×10 mL). The organic layer was dried with $MgSO_4$ and concentrated under reduced pressure. The product was purified on preparative silica TLC using a 4:1 mixture of $CH_2Cl_2$ and MeOH as a solvent. The yield of compound 5 was 60 mg (49%). $^1$H NMR (CDCl3) δ7.08 (bs, 1H), 5.61-5.45 (m, 2H), 3.92 (q, J=11.23 Hz, 2H), 3.64 (dd, J1=9.91 Hz, J2=4.73 Hz, 1H), 3.36 (q, J=6.07 Hz, 2H), 2.87 (bs, 2H), 2.31-2.16 (m, 4H), 2.08-2.04 (m, 1H), 1.89-1.49 (m, 5H). $^{13}$C NMR (CDCl$^3$) δ170.34, 135.48, 131.37, 75.80, 68.31, 41.28, 40.05, 34.28, 32.53, 29.74, 27.85. HRMS: m/z [M+H]$^+$ calcd. for $C_{12}H_{23}N_2O_2$ 227.1754, found 227.1791.

Figure 20:
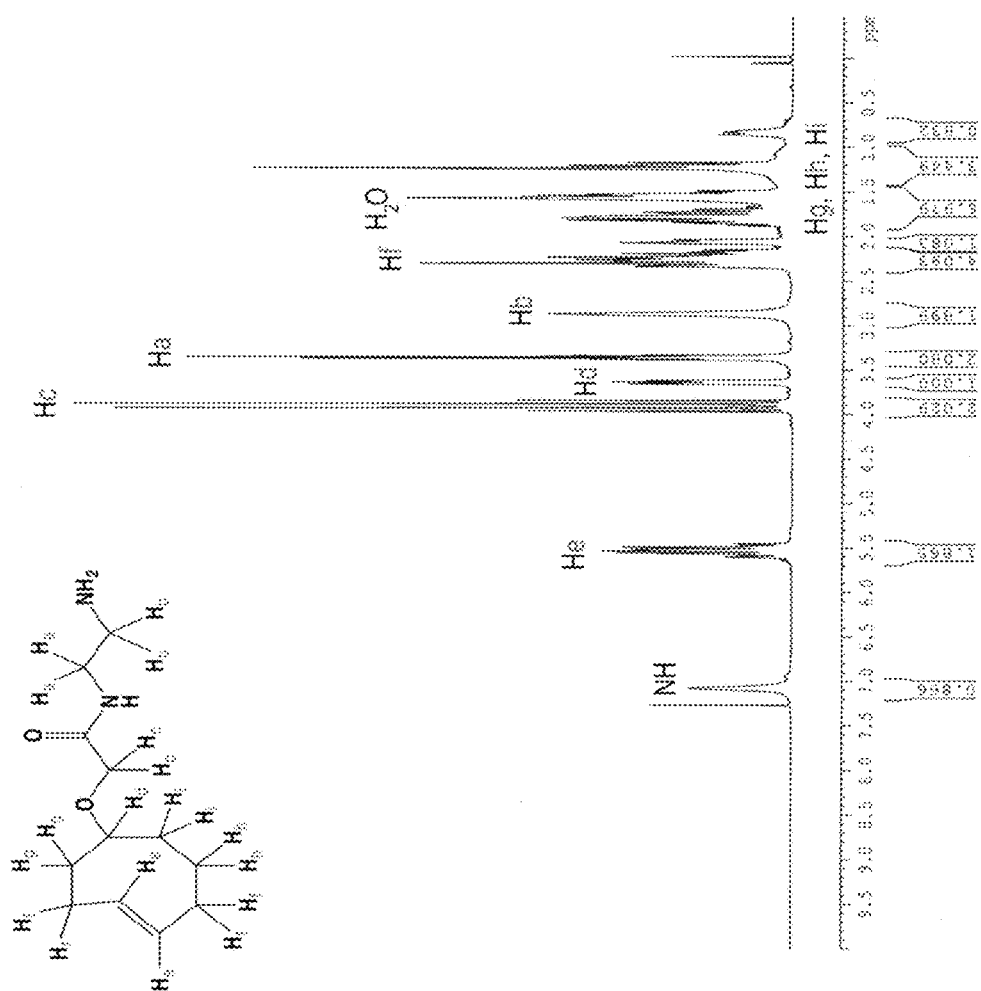
FIG. 20 shows the NMR for (R,E)-N-(2-aminoethyl)-2-(cyclooct-4-en-1-yloxy)acetamide (5).
Figure 21:
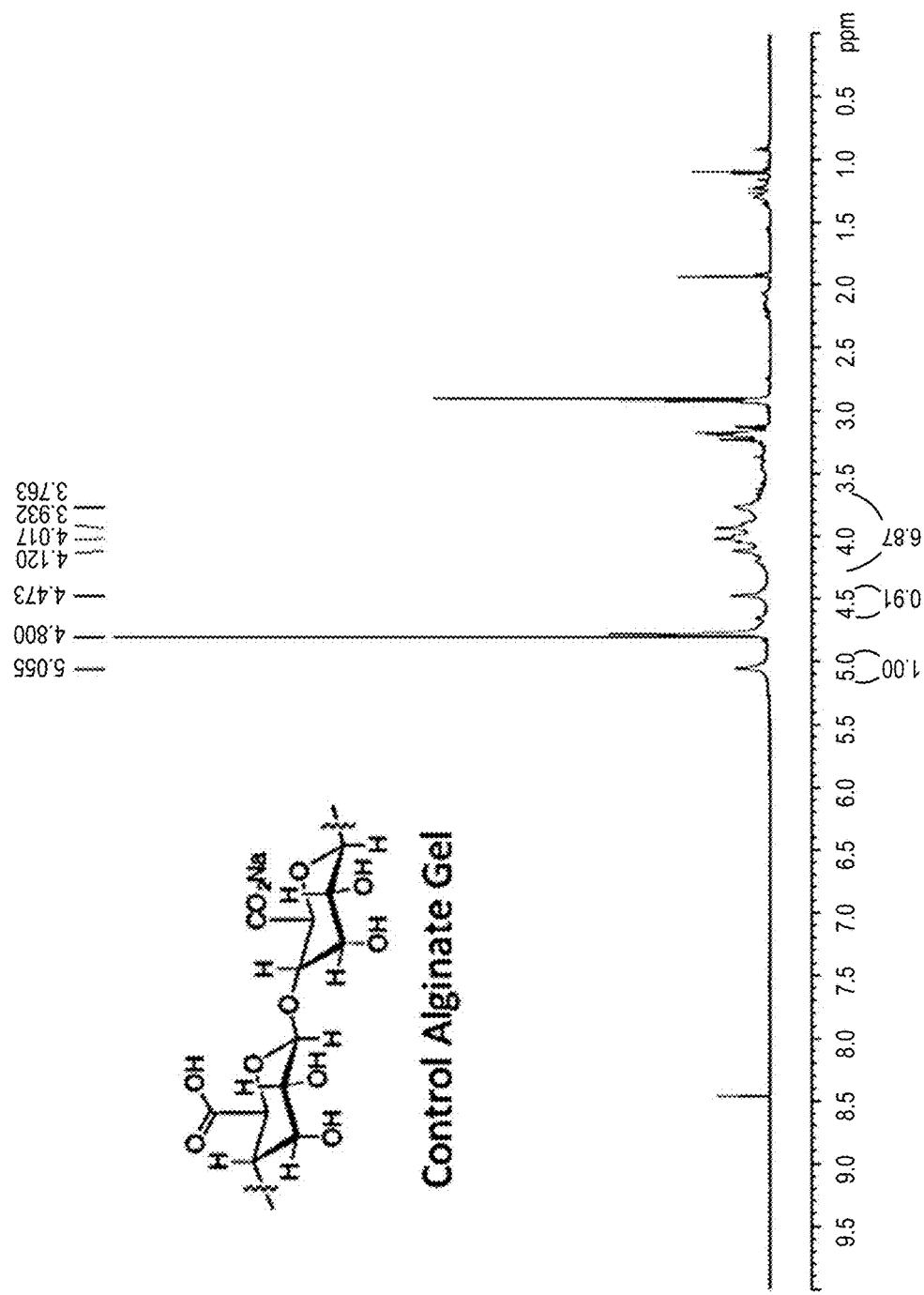
FIG. 21 shows the NMR for unmodified alginate gel.
Figure 22:
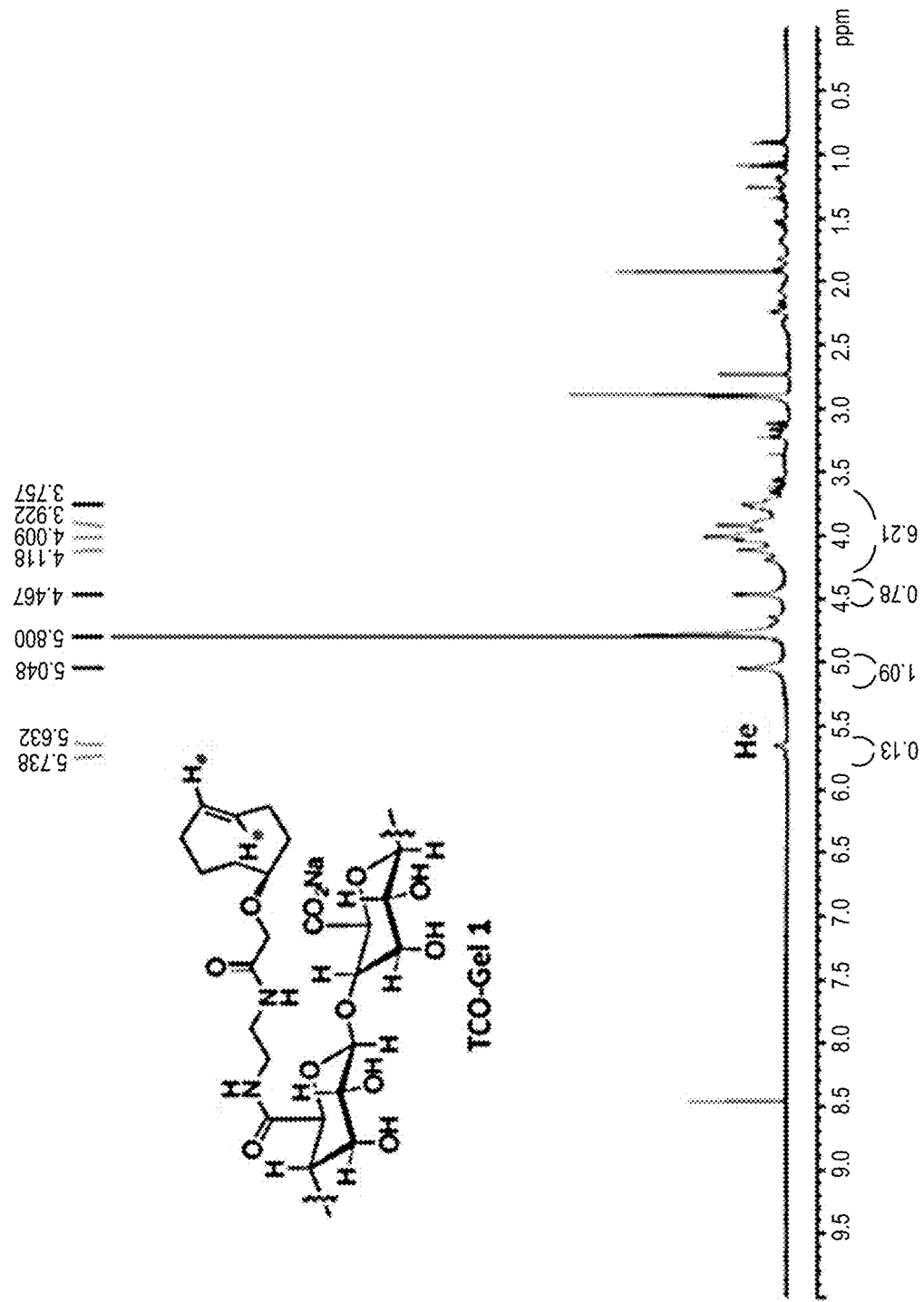
FIG. 22 shows the NMR for TCO-gel 1.

Each gram of UP MVG alginate was combined with 176 μmol of TCO-amine under standard carbodiimide chemistry conditions, as previously described for arginine-glycine-aspartic acid (RGD) and glycine-histidine-lysine (GHK) incorporation. The alginate product was then purified by dialysis against deionized water containing decreasing salt concentrations for 4 days, frozen and lyophilized for 5-10 days until dry. A 2.5% alginate solution was obtained by adding DPBS, and alginate gels were fabricated by the addition of calcium. Covalent modification of alginate was confirmed through 1H-NMR studies (see FIGS. 20-22). The same protocol without the TCO addition was used for the construction of control gels. The in vitro and in vivo studies were done with TCO-gel from the exact same batch and used on the same day to minimize any variations in loading amount or loading efficiency.

For in vitro experiments, 800 μl of 2.5% alginate solution was mixed with 200 μl of supersaturated Ca(SO4)2 solution (0.21 g of Ca(SO4)2 per ml of double-distilled water (ddH2O)). The solutions were mixed for 30 s using a three-way stopcock to achieve a final alginate concentration of 2%. The mixture was allowed to gel between two glass plates in a custom-made plastic model and incubated for 20 min at room temperature. The entire volume had a uniform appearance consistent with gelation. The discs were picked up with a spatula and weighed individually. Typically, a premade disc weighed approximately 100 mg and had roughly the following dimensions: 8 mm (diameter) and 2 mm (height).

For in vivo use, the 2.5% alginate gel solution and the super-saturated calcium sulfate solution were mixed rapidly in the same proportions as mentioned above and immediately injected to the animal in the desired amount.

Example 2

Preparation of Tetrazine-Modified Diagnostic Agent

Tz radioprobe 2 was synthesized as previously described (R. Rossin, P. R. Verkerk, S. M. van den Bosch, R. C. Vulders, I. Verel, J. Lub, M. S. Robillard, *Angew. Chem. Int. Ed. Engl.* 2010, 49, 3375).

Example 3

Preparation of (E)-cyclooct-2-Enyl 2-Aminoethylcarbamate

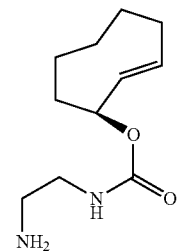

The title compound was prepared according to the procedure described in Versteegen, R. M. et. al., *Angew. Chem. Int. Ed.* 2013, 52, 14112-14116.

Example 4

Preparation of Releasable TCO-Modified Diagnostic Agent

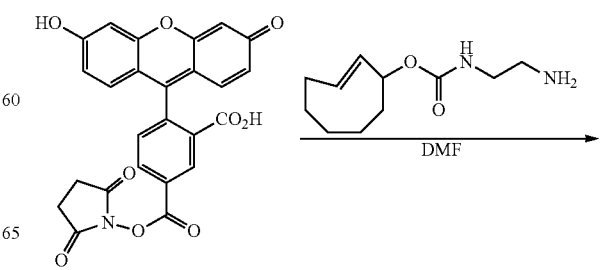

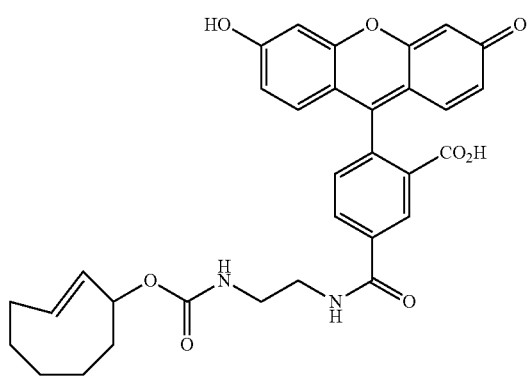

Dissolved fluorescein-NHS ester (134 mg, 0.283 mmol) and (Z)-cyclooct-2-enyl 2-aminoethylcarbamate (60.0 mg, 0.283 mmol) in DMF (5 mL). Added triethylamine (77 μL, 0.566 mmol) and stirred at rt for 18 h. Evaporated the solvent under high vacuum and redissolved the reaction mixture in methanol. Purified by preparatory thin layer chromatography using 1:9 MeOH:CH$_2$Cl$_2$ mixture as mobile phase. Yield=90 mg (55.6%). $^1$H NMR (CD$_3$OD, 400 MHz) δ8.42 (s, 1H), 8.17 (d, J=8.2 Hz, 1H), 7.25 (d, J=8.2 Hz, 1H), 6.86 (s, 2H), 6.57-6.50 (m, 4H), 5.78 (t, J=12.3 Hz, 1H), 5.47 (d, J=16.4 Hz, 1H), 5.2 (app s, 1H), 3.61-3.31 (m, 5H), 2.32 (bs, 1H), 1.98-1.88 (m, 3H), 1.83-1.77 (m, 1H), 1.69-1.04 (m, 5H), 0.83-0.75 (m, 1H). $^{13}$C NMR (CD$_3$OD, 100 MHz) δ168.74, 161.63, 158.85, 156.60, 154.17, 137.94, 135.62, 132.86, 132.70, 130.20, 125.81, 125.31, 113.89, 111.03, 103.81, 75.43, 41.69, 41.21, 37.08, 36.67, 30.14, 25.27. HRMS (ESI-MS) m/z: calcd. for C$_{32}$H$_{30}$N$_2$O$_8$ [M+H$^+$H$^+$] 571.2080; found 571.2025.

Example 5

Preparation of TCO-Modified Diagnostic Agent

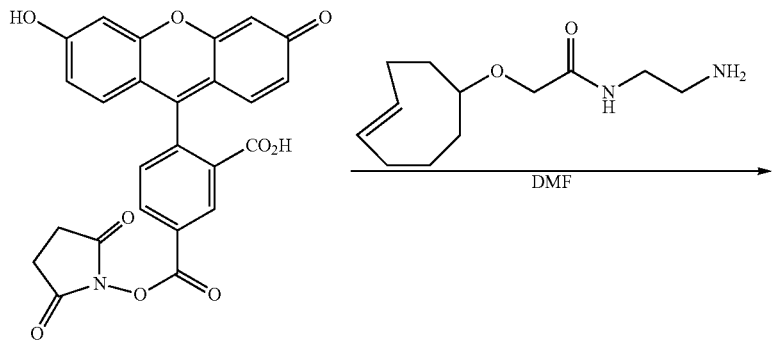

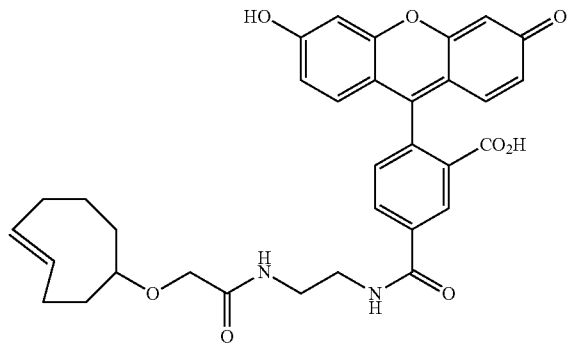

Dissolved 2-((E)-cyclooct-2-enyloxy)-N-(2-aminoethyl) acetamide (50.0 mg, 0.221 mmol) and fluorescein-NHS ester (105 mg, 0.221 mmol) in DMF (5 mL). Added triethylamine (60 μL, 0.442 mmol) and stirred at rt for 18 h. Evaporated the solvent under high vacuum and redissolved the reaction mixture in methanol. Purified by preparatory thin layer chromatography using 1:9 MeOH:CH$_2$C$_{12}$ mixture as mobile phase. Yield=51 mg (39.5%). $^1$H NMR (CD$_3$OD, 400 MHz) δ8.46 (s, 1H), 8.21 (d, J=8.2 Hz, 1H), 7.65 (bs, 1H), 7.28 (d, J=8.2 Hz, 1H), 6.69 (d, J=2.7 Hz, 2H), 6.58-6.50 (m, 4H), 5.46-5.44 (m, 2H), 3.91 (d, J=5.5 Hz, 2H), 3.65-3.59 (m, 5H), 2.67 (s, 1H), 2.32-2.26 (m, 2H), 2.32-2.26 (m, 2H), 2.20-2.13 (m, 1H), 2.08 (d, J=4.2 Hz, 1H), 1.96-1.92 (m, 1H), 1.79-1.67 (m, 3H), 1.54-1.46 (m, 1), 1.30-1.25 (m, 1H), 1.23-1.15 (m, 1H). $^{13}$C NMR (CD$_3$OD, 100 MHz) δ173.60, 170.67, 168.69, 154.21, 137.21, 137.66, 136.66, 136.75, 132.53, 130.30, 125.89, 125.09, 113.84, 110.98, 103.79, 77.56, 69.38, 41.31, 40.75, 40.07, 39.94, 35.50, 33.58, 30.82, 29.05. HRMS (ESI-MS) calcd. for C$_{33}$H$_{32}$N$_2$O$_8$ [M+H$^+$] 585.2237; found 585.2183.

Example 6

Preparation of Releasable TCO-Modified Amoxicillin

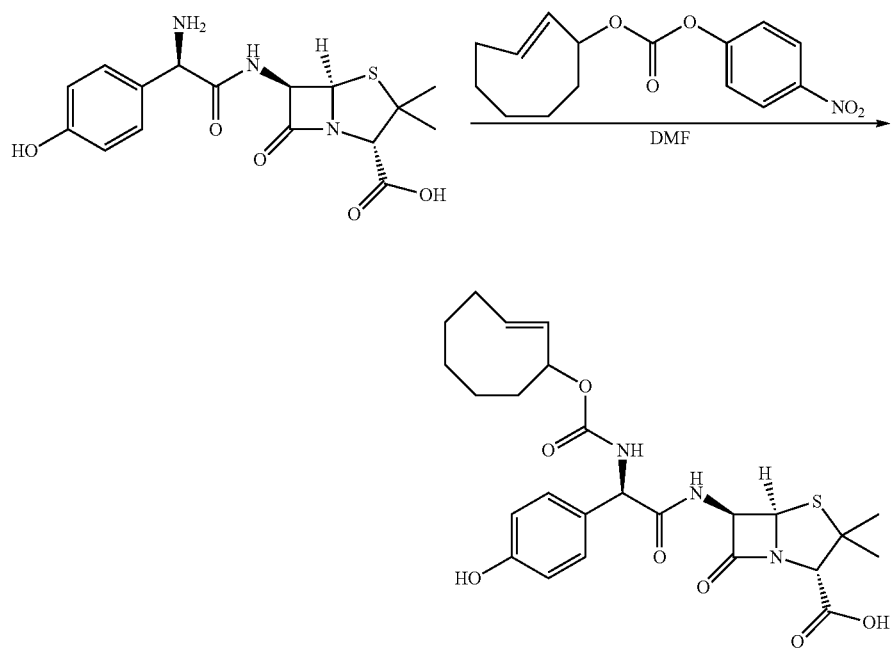

Dissolved (E)-cyclooct-2-enyl 4-nitrophenyl carbonate (100 mg, 0.343 mmol) and amoxicillin (82.0 mg, 0.224 mmol) in DMF (5 mL). Added triethylamine (87 μL, 0.634 mmol) and stirred at rt for 18 h. Evaporated the solvent under high vacuum and redissolved the reaction mixture in methanol. Purified by preparatory thin layer chromatography using 1:9 MeOH:CH$_2$Cl$_2$ mixture as mobile phase. Yield=36 mg (31%). $^1$H NMR (CD$_3$OD, 400 MHz) δ8.49 (bs, 1H), 7.57 (dd, J$_1$=21.8 Hz, J$_2$=8.2 Hz, 1H), 7.24 (d, J=6.8 Hz, 2H), 6.67 (d, J=6.9 Hz, 2H), 5.81-5.76 (m, 1H), 5.51 (d, J=16.4 Hz, 1H), 5.29 (s, 1H), 5.17 (s, 1H), 4.92 (s, 1H), 4.33 (s, 1H), 3.62 (s, 3H), 3.38 (s, 1H), 2.50 (s, 2H), 2.38 (bs, 1H), 1.98-1.88 (m, 3H), 1.81-1.75 (m, 1H), 1.64-1.53 (m, 2H), 1.37 (s, 3H), 1.19-1.12 (m, 4H), 0.81-0.78 (m, 2H). $^{13}$C NMR (CD$_3$OD, 100 MHz) δ170.49, 156.77, 154.78, 132.16, 131.87, 131.24, 130.95, 128.60, 114.83, 72.99, 65.73, 59.77, 59.07, 57.53, 57.03, 56.89, 51.93, 48.60, 35.54, 35.31, 28.46, 27.07, 26.76, 23.67, 23.54. HRMS (ESI-MS) m/z: calcd. for C$_{33}$H$_{32}$N$_2$O$_8$ [M+MeO$^-$] 548.2072; found 548.2042.

Example 7

Preparation of TCO-Modified Amoxicillin

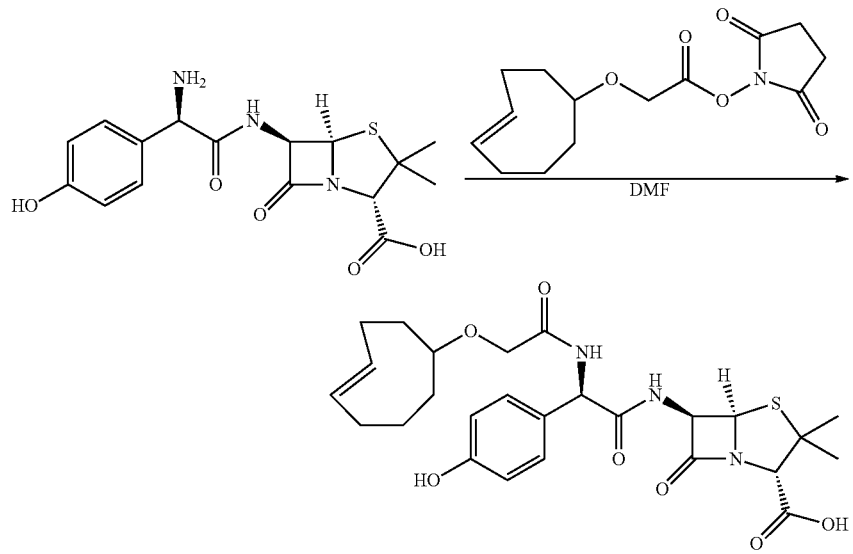

Dissolved 2-((E)-cyclooct-2-enyloxy)acetic acid (85.0 mg, 0.461 mmol), N-hydroxysuccinamide (53.0 mg, 0.461 mmol) and N,N'-dicyclohexylcarbodiimide (95.0 mg, 0.461 mmol) in $CH_2Cl_2$ (5 mL). Stirred at rt for 18 h. The precipitate was filtered and the supernatant was concentrated under reduced pressure. Added a solution of amoxicillin (160 mg, 0.438 mmol) in DMF (10 mL) and stirred at rt for 18h. Evaporated the solvent under high vacuum and redissolved the reaction mixture in methanol. Purified by preparatory thin layer chromatography using a 1:9 MeOH:$CH_2Cl_2$ mixture as mobile phase. Yield=20 mg (8.6%). $^1$H NMR ($CD_3OD$, 400 MHz) δ7.33 (t, J=9.5 Hz, 1H), 7.24 (t, J=0.6 Hz, 1H), 6.76 (d, J=8.2 Hz, 2H), 5.68-5.45 (m, 4H), 4.32 (bs, 1H), 3.99-3.09 (m, 2H), 3.72 (s, 1H), 3.47 (bs, 1H), 2.67 (s, 6H), 2.37-1.96 (m, 5H), 1.85-1.80 (m, 3H), 1.56 (s, 3H), 1.47 (s, 3H), 1.28-1.17 (m, 3H). $^{13}$C NMR ($CD_3OD$, 100 MHz) δ175.08, 172.65, 171.82, 158.81, 131.16, 131.07, 130.69, 130.13, 129.98, 129.89, 116.69, 83.19, 68.67, 66.71, 59.88, 58.86, 57.05, 53.13, 35.26, 35.14, 34.26, 34.19, 27.18, 26.75, 26.69, 26.41, 23.44, 23.41. HRMS (ESI-MS) m/z: calcd. for $C_{33}H_{32}N_2O_8$ [M+MeO$^-$] 548.2072; found 548.2042.

Example 8

Preparation of Modified Agarose

Figure 16A:
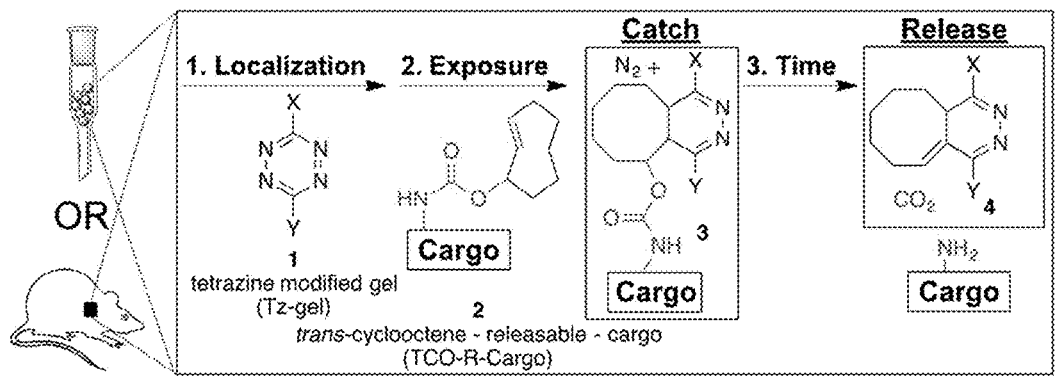
FIG. 16A and FIG. 16B shows the method of the present invention using the catch-and-release linker. Briefly, the method involves first the localization of a solid carrier modified with click chemistry carrier, in this particular instance tetrazine. Then a cargo modified with a carbamate (green) and a trans-cyclooctene moiety is exposed to the material (either in-vitro or in-vivo). Both reagents react in-situ and depending on the substituents of the tetrazine the cargo is either released from or immobilized to the solid carrier.
Figure 16B:
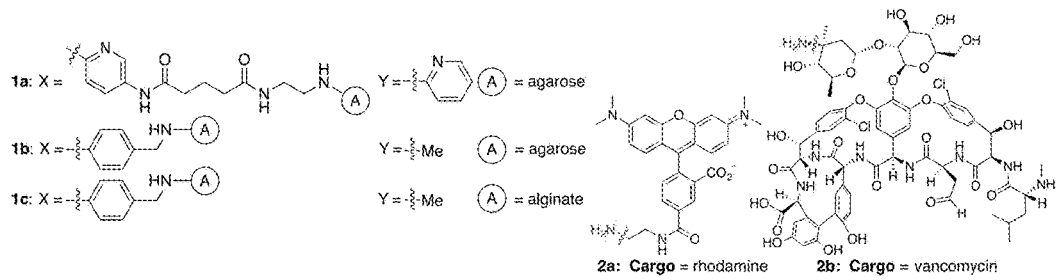
Figure 17:
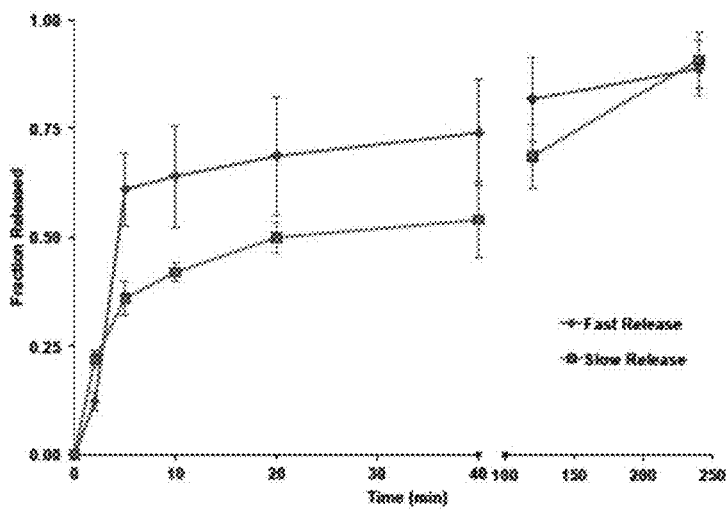
FIG. 17 shows the release kinetics of TCO-R-Rhodamine after exposure to agarose beads modified with different tetrazines. Briefly, Agarose 1a with heterocyclic substituents at X & Y as shown in FIG. 16, leads to a slow release (red line), presumably due to attenuating by electron withdrawing groups. On the other hand, an aromatic substituent at X & an alkyl substituent at Y lead to fast release of Rhodamine diethyl amine. The values are the result of triplicates.

The NHS-activated agarose spin columns were purchased from Pierce/Thermo Fisher Scientific (Rockford, Ill.). The amine precursors to 1a or 1b of FIG. 16B were coupled to the agarose beads using the manufacturer's recommended protocol. Briefly, 33 mg of dry agarose was incubated with 4 μmol of the amine precursor of 1a or 1b in PBS buffer pH 7.4 for 3 h with gentle mixing. The agarose beads were washed several times with PBS. The amount of 1a or 1b bound to the column was estimated by monitoring the absorbance at 520 nm of the supernatants obtained from the washes. The unreacted NHS groups on agarose were capped with 1 M Tris, pH 7.4.

Example 9

Kinetics of Catch & Release Linker

The agarose beads modified with either 1a or 1b, using the method described above, were treated with 2 μmol of TCO-R-Rhodamine ((E)-5-((2-(((cyclooct-2-en-1-yloxy)carbonyl)amino)ethyl)carbamoyl)-2-(3-(dimethyl-□$^4$-azanydene)-6-(dimethylamino)-3H-xanthen-9-yl)benzoic acid) for 2 min. The supernatant was collected after a quick centrifugation and the agarose was resuspended in water. The supernatents were collected at regular time intervals and analyzed by ESI-MS.

The samples were analyzed on a Thermo Fisher Scientific (West Palm Beach, Calif.) LTQ Orbitrap Velos Mass spectrometer, using quartz capillary emitters. To facilitate spray optimization, 10% isopropyl alcohol was added to each sample prior to MS analysis. The release product, Rhodamine ethyl diamine (5-((2-aminoethyl)carbamoyl)-2-(3-(dimethyl-□$^4$-azanylidene)-6-(dimethylamino)-3H-xanthen-9-yl)benzoic acid), was analyzed in the positive mode. The release product rhodamine ethyl diamine was independently synthesized for ESI-MS calibration (FIG. SX). The calibration curve was used to estimate the amount of rhodamine ethyl diamine in the supernatants of each step.

Example 10

Preparation of Modified Tz-Me-Alginate

Figure 23:
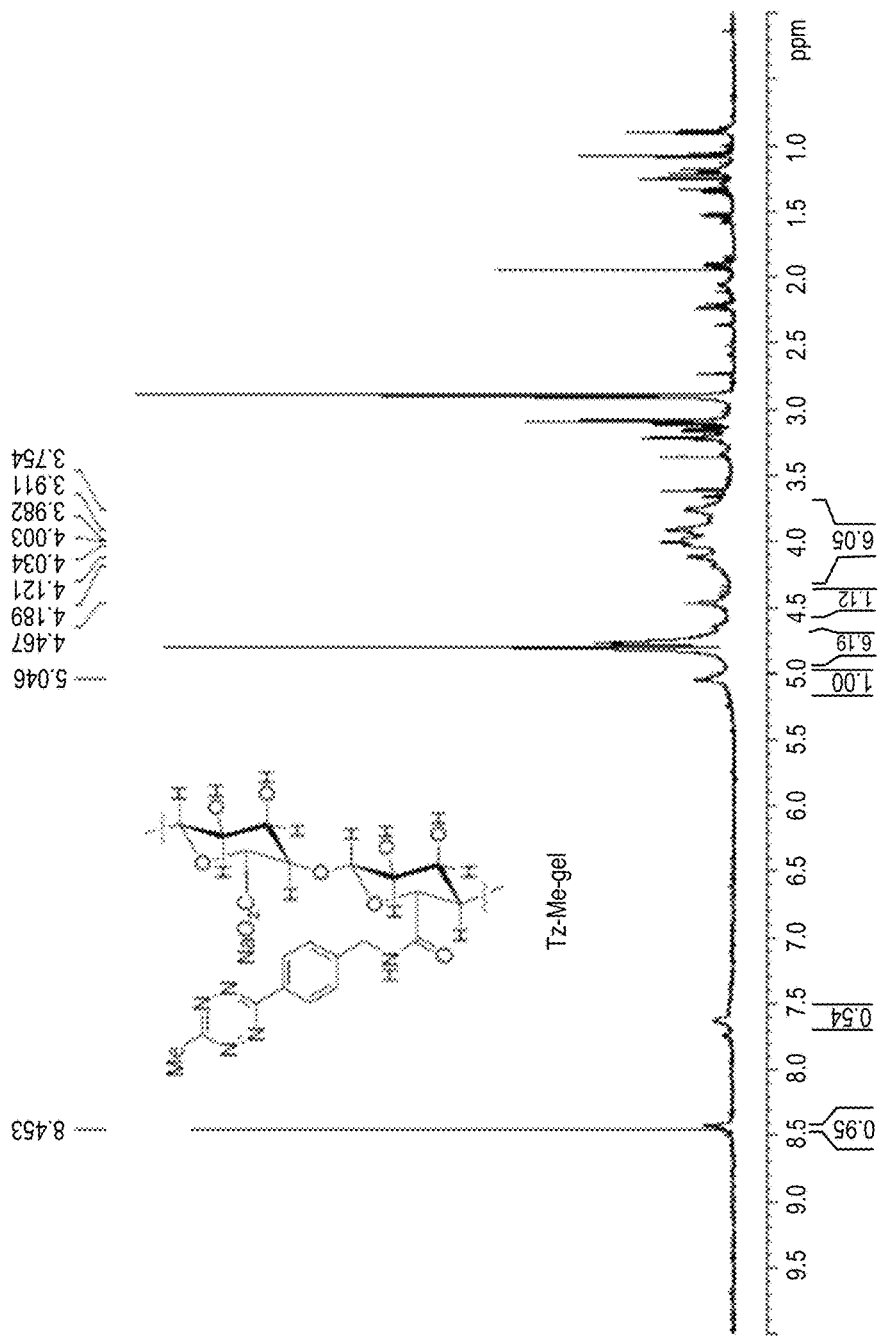
FIG. 23 shows the NMR for Tz-Me-gel.
Figure 24:
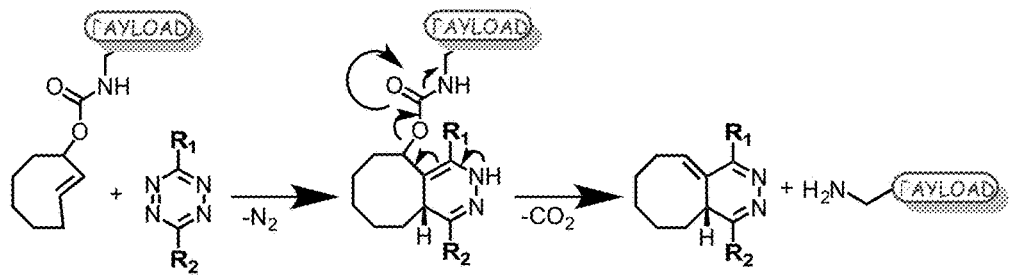
FIG. 24 shows "Catch & Release" strategy, employing bio-orthogonal TCO-tetrazine chemistry.
Figure 25:
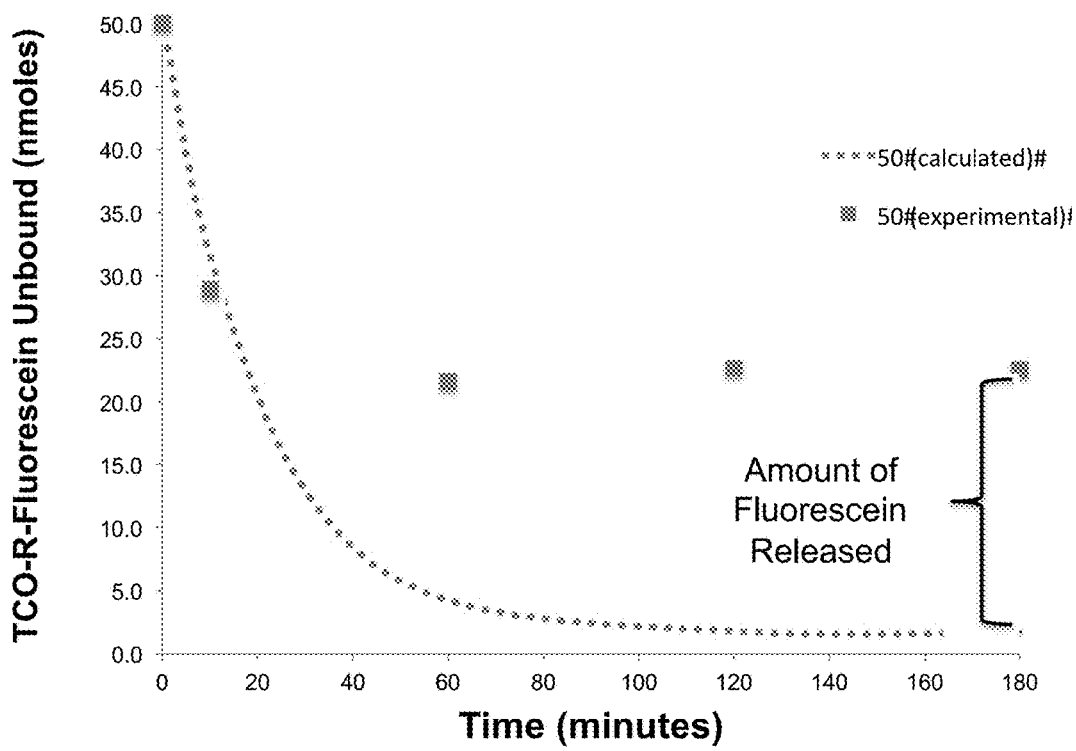
FIG. 25 shows the amount of flourescein released after 180 minutes. This is calculated as the difference between the expected value of bound fluorophore and the actual experimental value obtained.
Figure 26:
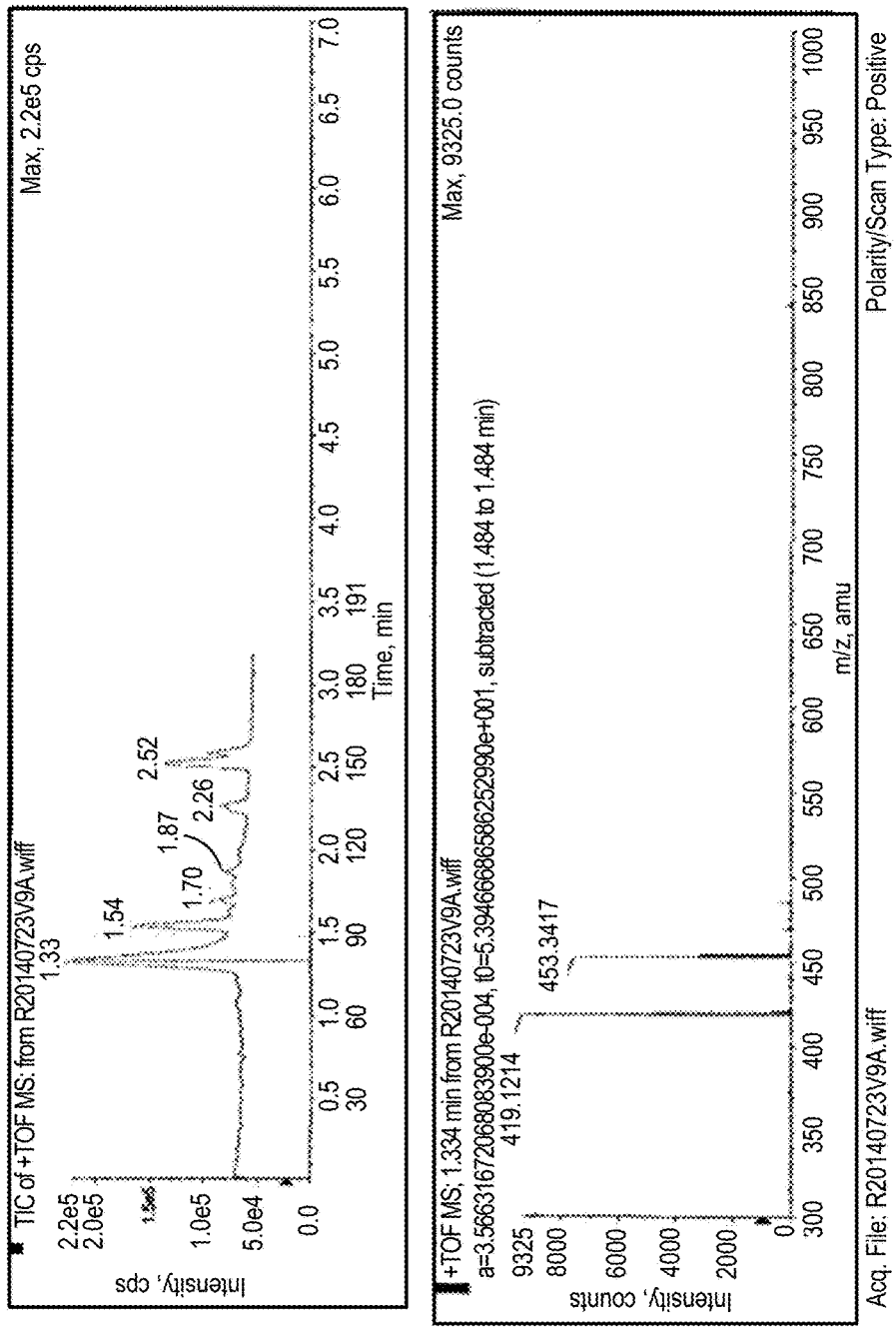
FIG. 26 shows peaks of fluorescein diamine ([M+H] 419.1214 & [M+MeOH]453.3417) found on supernatant from the mixture of Tz-Me-gel and TCO-R-Fluorescein after 60 minutes, confirming the expected "catch & release" product by Liquid Chromatography—Mass Spectrometry.
Figure 27:
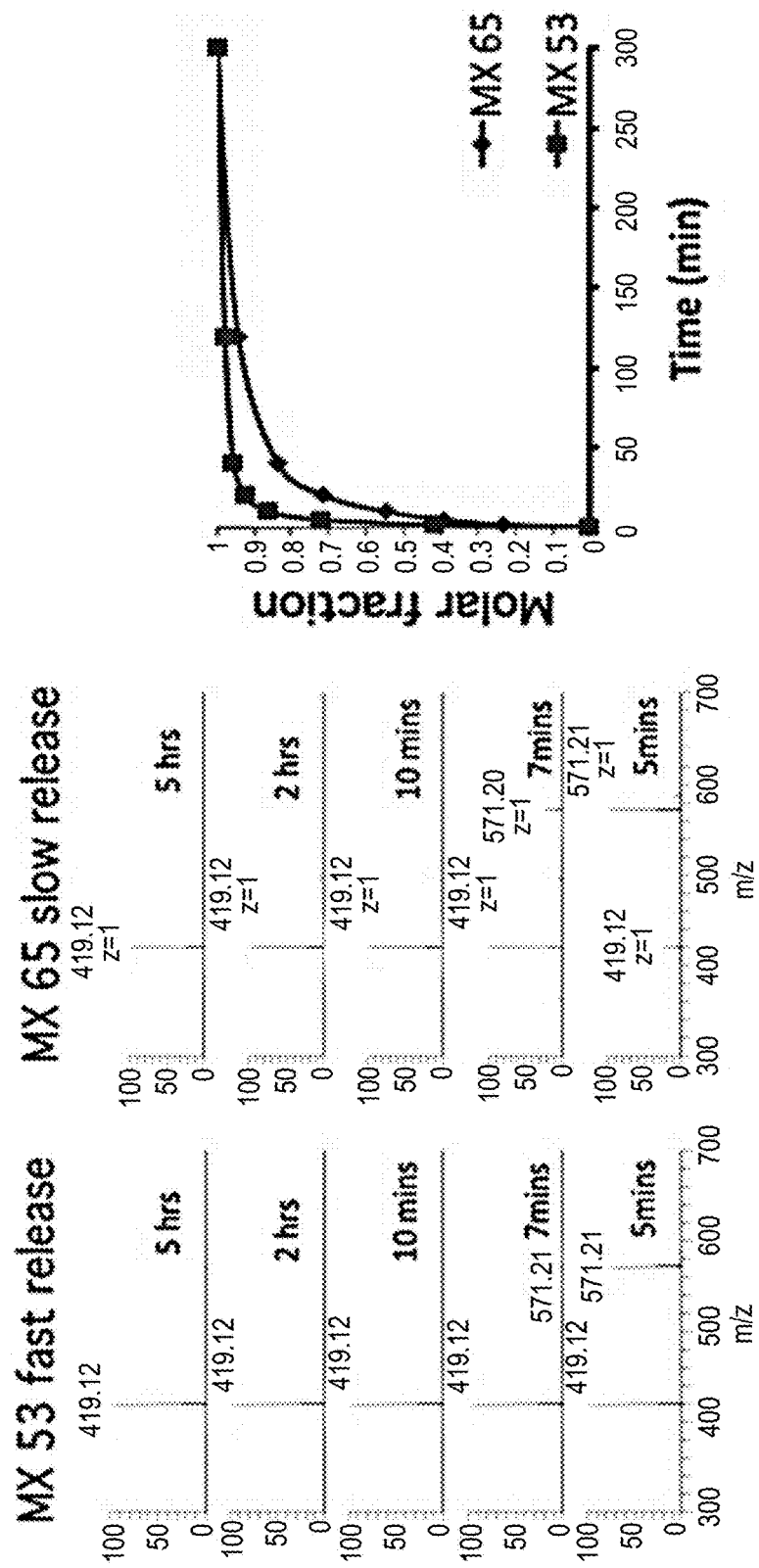
FIG. 27 shows the release kinetics of TCO-R-Fluorescein ([M+H] is 571.21) after exposure to agarose beads modified with different tetrazines. Briefly, Agarose 1a with heterocyclic substituents at X & Y as shown in FIG. 16, leads to a slow release (MX53, red line), presumably due to attenuating by electron withdrawing groups. On the other hand, an aromatic substituent at X & an alkyl substituent at Y lead to fast release of Rhodamine diethyl amine (MX65, blue line). The left hand side shows a dynamic evaluation of the release through mass spectroscopy.
Figure 28:
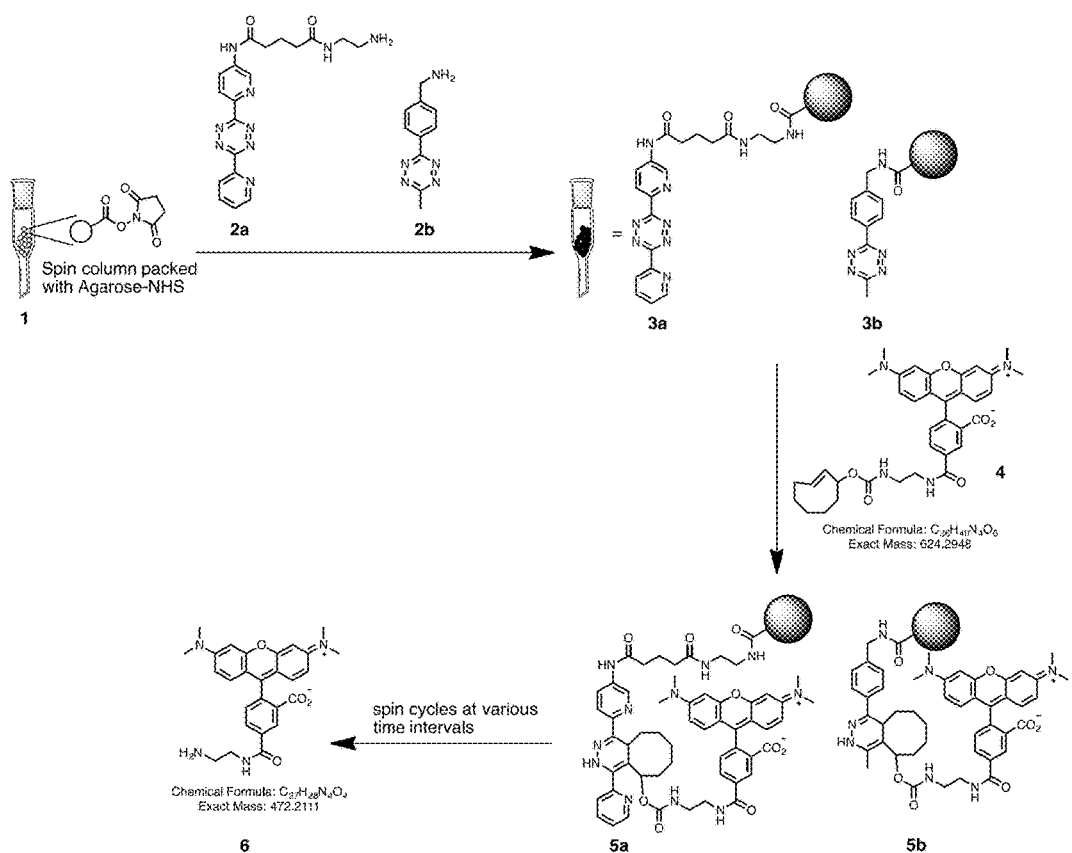
FIG. 28 shows setup for the kinetic study of 'Catch & release' of fluorescein-labeled TCO from tetrazine-modified agarose.
Figure 29:
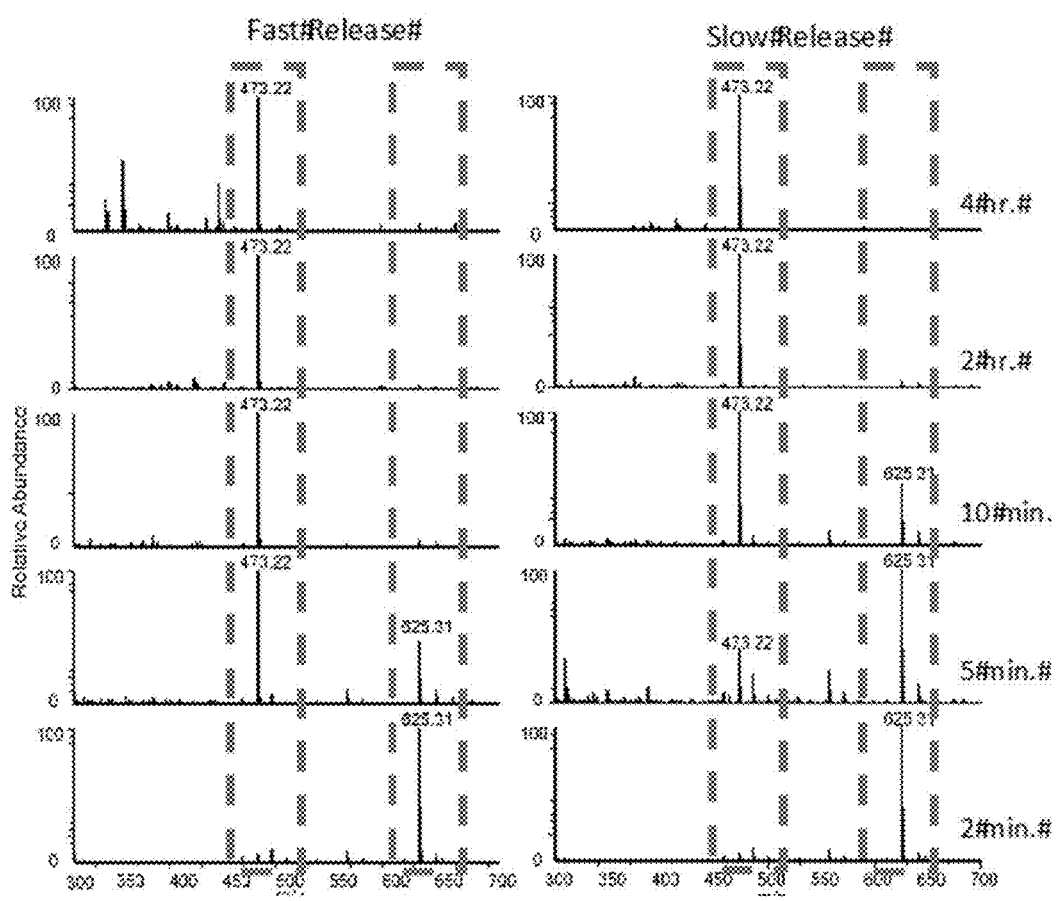
FIG. 29 shows a dynamic evaluation of the release of TCO-R-Rhodamine ([M+H]625.31) through mass spectroscopy. The release product is found as expected at 473.22.
Figure 30:
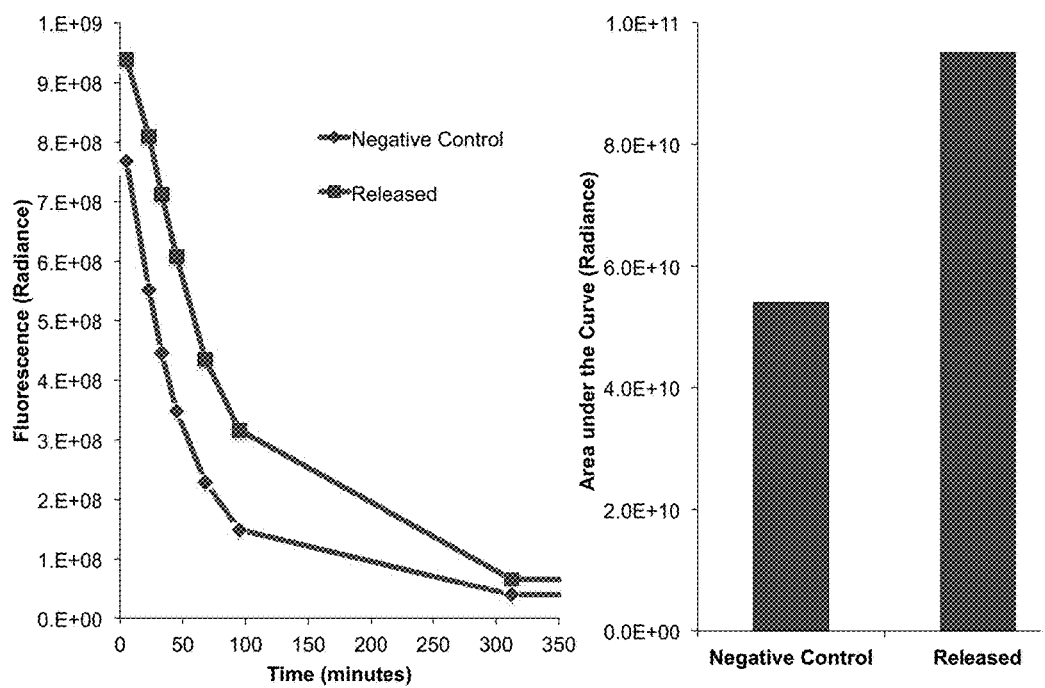
FIG. 30 shows the increase in fluorescence based on the previous kinetic biodistribution study at each time point comparing negative control (no gel injection) vs the release protocol (Tz-Me-Gel) after injection of TCO-R-Rhodamine. The bar graph extrapolates the data to a presumed total amount achieved in 8 hours. The dose reflected by the area under the curve is almost doubled in the presence of the gel as shown in the "released" column (right) vs the negative control (left).
Figure 31:
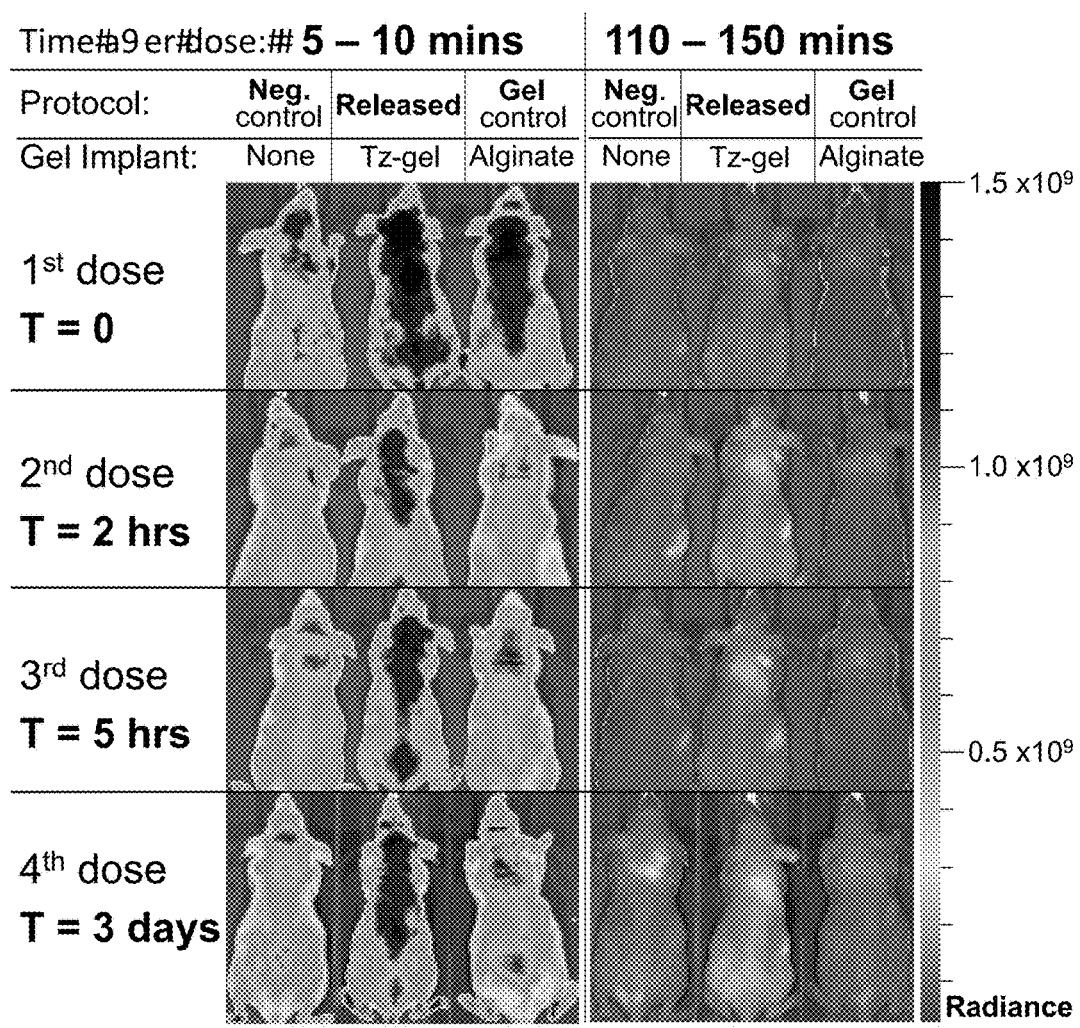
FIG. 31 shows kinetic multiple dose evaluation of mice. Three mice were evaluated after each injection of 50 nmoles of TCO-R-Rhodamine through tail vein injection. The mice were treated as described above their images. The "negative control" subject did not receive any gel injection. The "released" subject received an injection in the subcutaneous back of Tz-Me-gel. The "gel control" subject received an injection in the subcutaneous back of alginate gel. The mice were evaluated with an IVIS Spectrum machine after 5-10 minutes and 110-150 minutes after each dose of fluorophore.
Figure 32:
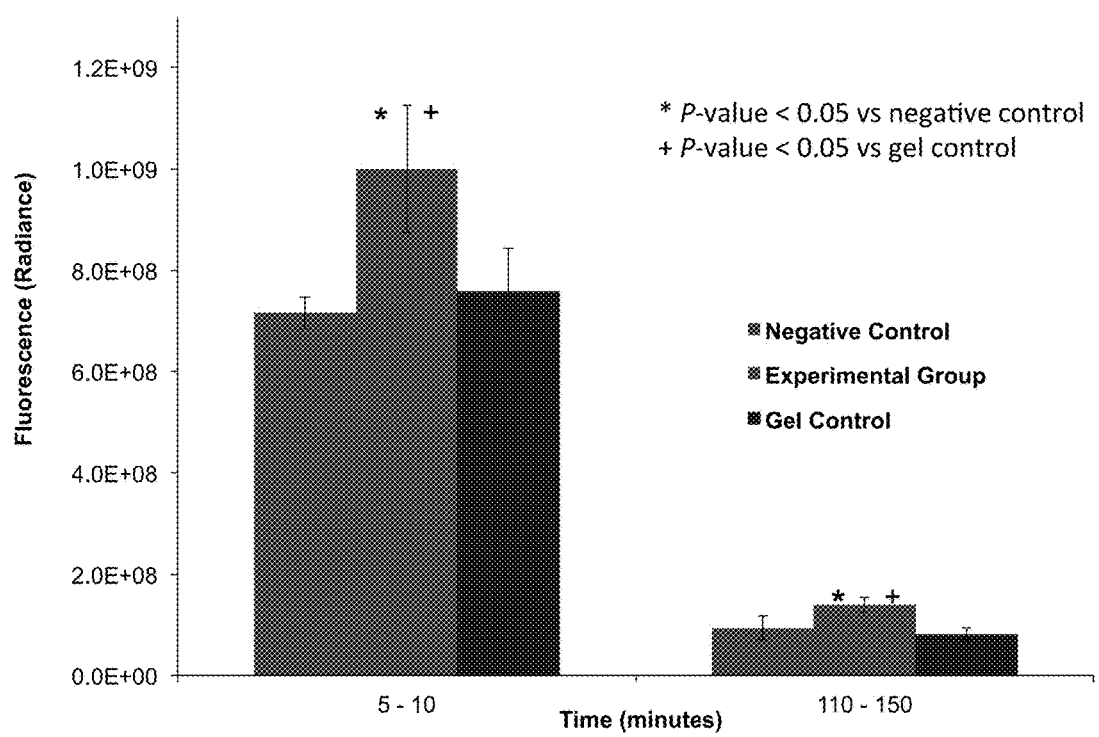
FIG. 32 shows the average fluorescence observed at 5-10 minutes vs 110-150 minutes after the second, third & fourth injection with 50 nmoles of TCO-R-Rhodamine to each of the different experimental groups (negative control=no gel; experimental group=Tz-Me-gel; gel control=unmodified alginate gel). The fluorescence is statistically higher in the experimental group than either in the negative or gel control groups. Compared by paired T-test (n=3).

Each gram of UP MVG alginate was combined with 176 μmoles of (4-(6-Methyl-1,2,4,5-tetrazin-3-yl)phenyl)methanamine (Tz-Me-amine) under standard carbodiimide chemistry conditions as previously described for RGD, GHK and TCO amine incorporation. Then the alginate product was purified by dialysis against deionized water containing decreasing salt concentrations for 4 days, frozen and lyophilized for 5-10 days until dry. A 2.5% alginate solution was obtained by adding ddH₂O, and alginate gels were fabricated by the addition of calcium. Covalent modification of alginate was confirmed through 1H-NMR studies (see FIG. 23). The same protocol without the TCO addition was used for the construction of control gels. The in-vitro and in-vivo studies were done with TCO-Gel 1 from the exact same batch and used on the same day to minimize any variations in loading amount or loading efficiency.

For in-vivo experiments, 800 μl of 2.5% alginate solution were mixed with 200 μl of supersaturated Ca(SO₄)₂ solution (0.21 g Ca(SO₄)₂/ml ddH₂O). The solutions were mixed for 30 s using a three-way stopcock to achieve a final alginate concentration of 2%. The mixture was immediately injected to the animal in the desired amount.

Example 11

In-vivo Evaluation of Catch & Release Linker

After IACUC approval, in-vivo real-time biodistribution studies of fluorescence were carried out in nu/nu mice (n=2 per condition) by injecting either nothing or a type of alginate (control vs Tz-Gel). Then subjects received a tail-vein injection of TCO-R-F or TCO-NR-F. The negative controls were: 1. No gels with TCO-R-F (Negative control, mouse 1); 2. control alginate with TCO-R-F (Gel control, mouse 4). The two experimental groups were Tz-gel and either TCO-R-F (Released protocol, mouse 2) or TCO-NR-F (Immobilized protocol, mouse 3). Fluorescence was measured with an IVIS Spectrum (Perkin Elmer, Mass.) and reported in radiance.

Example 12

Minimum Inhibitory Concentration (MIC) of Releasable Vancomycin

We created serial dilutions of vancomycin or TCO-R-Vanco with either a regular alginate gel or Tz-gel overnight in ddH₂O. The following day luminescent methicillin sensitive *Staph. aureus* (MSSA, Xen 29, Perkin Elmer, Mass.) in 2.2% Mueller Winto broth were added to the mixture. The plates were then placed in the incubator for 24 and allowed to grow for 24 hours (n=3). Then luminescence was measured with an IVIS Spectrum (Perkin Elmer, Mass.) and reported in radiance.

Example 13

Preparation of Releasable TCO-Rhodamine

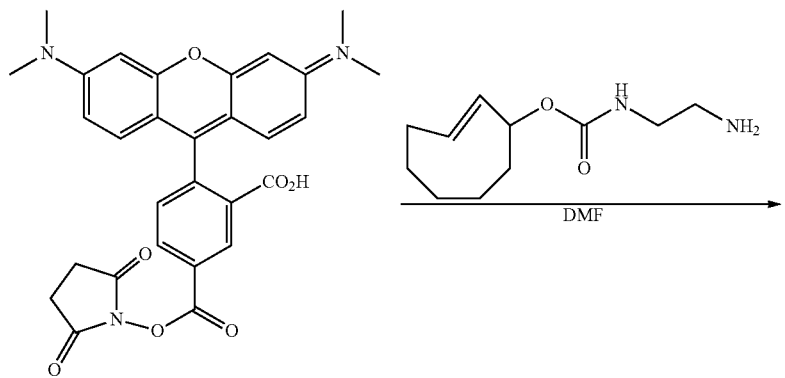

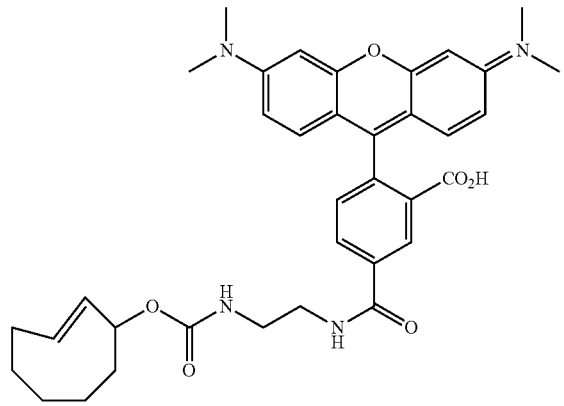

The Rhodamine-NHS ester was synthesized as described by Brunet, A.; Aslam, T.; Bradley, M. *Bioorg. Med. Chem. Lett.* 2014, 24, 3186-3188. Dissolved rhodamine-NHS ester (50 mg, 0.095 mmol) and (E)-cyclooct-2-enyl-2-aminoethylcarbamate (40.0 mg, 0.190 mmol) in CH2Cl2 (5 mL). Added triethylamine (129 μL, 0.95 mmol) and stirred at rt for 18 h. Evaporated the solvent under high vacuum and redissolved the reaction mixture in methanol. Purified by preparatory thin layer chromatography using 7.5:2.5:90 MeOH:Et3N:CH2Cl2 mixture as mobile phase. Yield=28 mg (47%). $^1$H NMR (CD$_3$OD, 400 MHz) δ8.54 (s, 1H), 8.04 (d, J=8.2 Hz, 1H), 7.34 (d, J=8.2 Hz, 1H), 7.23 (d, J=9.6 Hz, 1H), 6.99 (dd, J1=2.7 Hz, J2=9.5 Hz, 1H), 6.89 (d, J=2.8 Hz, 1H), 5.85 (t, J=13.7 Hz, 1H), 5.55 (d, J=16.4 Hz, 1H), 5.26 (s, 1H), 3.67-3.36 (m, 4H), 3.32-3.21 (m, 9H), 2.93-2.77 (m, 6H), 2.49-2.36 (m, 1H), 2.10-1.79 (m, 5H), 1.78-1.41 (m, 4H), 1.39-1.25 (m, 1H), 1.22-1.06 (m, 10H), 0.93-0.79 (m, 1H). $^{13}$C NMR (CD3OD, 100 MHz) δ172.47, 169.41, 161.68, 159.08, 158.76, 142.06, 137.19, 132.96, 132.70, 130.90, 129.85, 129.63, 115.09, 114.86, 97.53, 76.85, 75.38, 41.96, 41.78, 41.01, 37.18, 36.92, 30.21, 25.35. HRMS (ESI) m/z: calcd. for C36H41N4O6 [M+1]+625.3026; found 625.2976.

Example 14

Preparation of Non-Releasable TCO-Rhodamine

Dissolved rhodamine-NHS ester (50 mg, 0.095 mmol) and 2-((E)-cyclooct-4-enyloxy)-N-(2-aminoethyl)acetamide (43.0 mg, 0.190 mmol) in CH2Cl2 (5 mL). Added triethylamine (129 uL, 0.95 mmol) and stirred at rt for 18 h. Evaporated the solvent under high vacuum and redissolved the reaction mixture in methanol. Purified by preparatory thin layer chromatography using 7.5:5:2.5:90 MeOH:Et$_3$N:CH$_2$Cl$_2$ mixture as mobile phase. Yield=35 mg (58%). 1H NMR (CD$_3$OD, 400 MHz) δ8.57 (s, 1H), 8.07 (d, J=8.2 Hz, 1H), 7.34 (d, J=8.2 Hz, 1H), 7.22 (d, J=8.2 Hz, 2H), 6.97 (dd, J1=2.7 Hz, J2=9.6 Hz, 2H), 6.88 (d, J=2.7 Hz, 2H), 5.61-5.43 (m, 2H), 3.94 (d, J=4.1 Hz, 2H), 3.69-3.55 (m, 6H), 3.31 (s, 2H), 2.41-2.31 (m, 2H), 2.27-2.14 (m, 2H), 2.03-1.95 (m, 1H), 1.90 (s, 2H), 1.84-1.71 (m, 4H), 1.61-1.50 (m, 2H). 13C NMR (CD$_3$OD, 100 MHz) δ173.49, 172.35, 169.46, 161.47, 159.04, 158.71, 142.12, 136.97, 136.88, 132.70, 132.57, 129.84, 129.65, 115.02, 114.83, 97.55, 77.65, 69.44, 41.40, 41.00, 35.58, 33.62, 30.88, 29.10. HRMS (ESI) m/z: calcd. for C37H43N4O6 [M+1]+ 639.3183; found 639.3151.

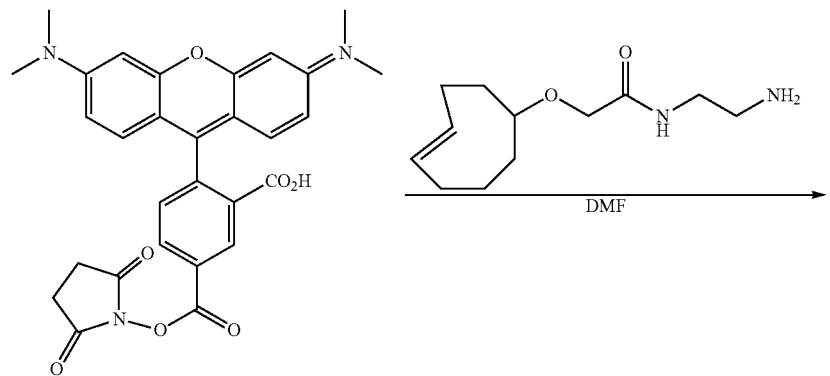

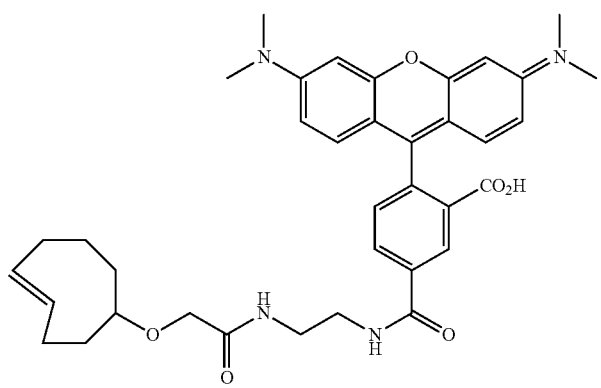

Example 15

Rhodamine Release Product

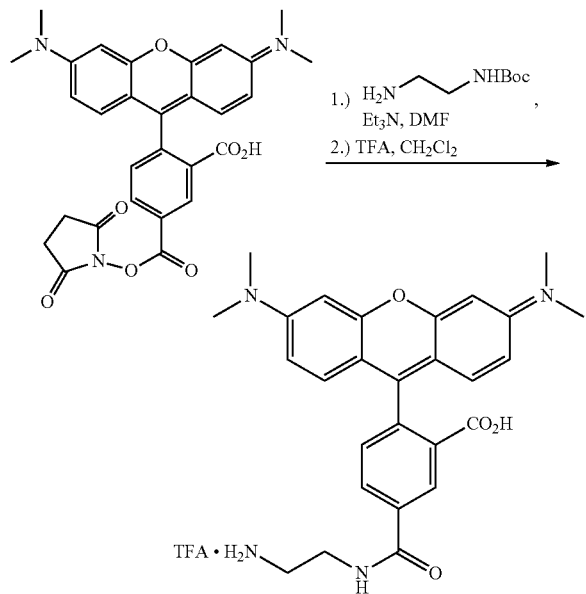

Dissolved rhodamine-NHS ester (20.0 mg, 0.0379 mmol) and N-Boc-ethylenediamine (13.2 mg, 0.0758 mmol) in $CH_2Cl_2$ (5 mL). Added triethylamine (51 μL, 0.379 mmol) and stirred at rt for 18 h. Evaporated the solvent under high vacuum and redissolved the reaction mixture in methanol. Purified by preparatory thin layer chromatography using 10:5:85 $MeOH:Et_3N:CH_2Cl_2$ mixture as mobile phase. The isolated product was treated with a 4:1 mixture of $CH_2Cl_2$:TFA (5 mL) for 1 h. Yield=18 mg (81%). $^1$H NMR ($CD_3OD$, 400 MHz) ™8.83 (s, 1H), 8.32 (d, J=9.6 Hz, 1H), 7.55 (d, J=8.1 Hz, 1H), 7.13 (d, J=9.6 Hz, 2H), 7.05 (dd, $J_1$=6.8 Hz, $J_2$=2.7 Hz, 2H), 6.96 (d, J=2.7 Hz, 2H), 3.77 (t, J=5.4 Hz, 2H), 3.30 (s, 12H), 3.22-3.17 (m, 2H). $^{13}$C NMR ($CD_3OD$, 100 MHz) ™169.28, 167.47, 160.69, 159.10, 138.52, 132.63, 132.11, 132.02, 131.67, 115.71, 114.85, 97.63, 41.08, 40.97, 39.06. HRMS (ESI) m/z: calcd. for $C_{27}H_{29}N_4O_4$ [M+1]+473.2189; found 473.2141.

Example 16

Releasable TCO-Vancomycin

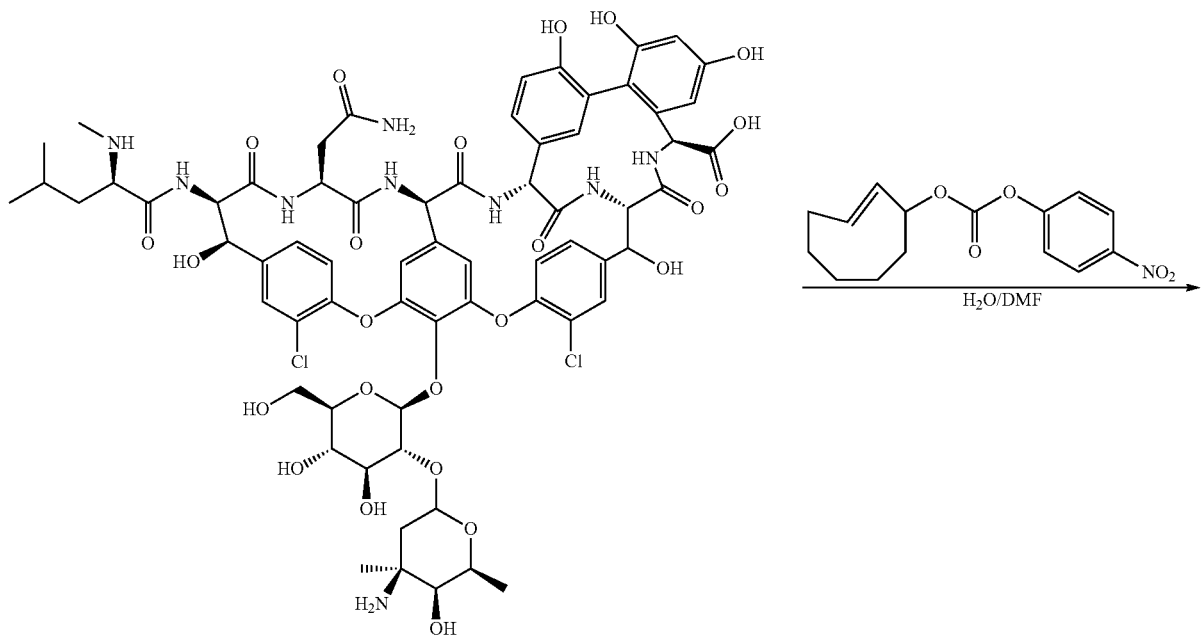

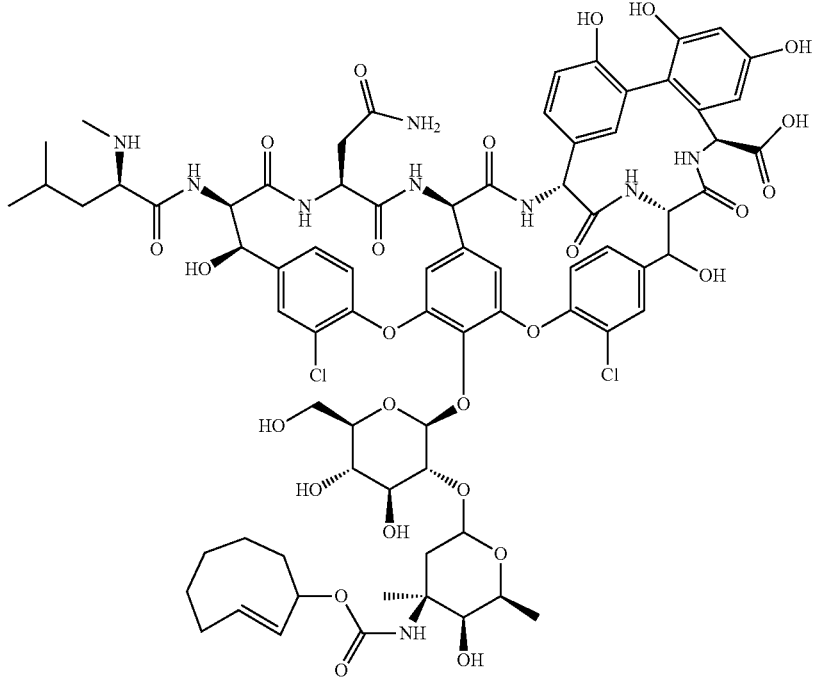

Dissolved vancomycin (50.0 mg, 0.0345 mmol) and triethylamine (20 μL, 0.145 mmol) in water (1 mL). Added a solution of (E)-cyclooct-2-enyl 4-nitrophenyl carbonate (19.0 mg, 0.0652 mmol) in DMF (25 μL). Stirred the reaction mixture at 40° C. for 18 h. Filtered out the precipitate through a 45 μm PTFE membrane. The supernatant was subjected to HPLC purification to obtain the title compound. A gradient of 10-60% CH3CN in H2O was used for the HPLC purification. Yield=3 mg (5.5%). 1H NMR (CD3OD, 400 MHz) δ7.61 (s, 1H), 7.55-7.38 (m, 2H), 7.19 (bs, 1H), 7.03 (s, 1H), 6.81 (bs, 1H), 6.44 (s, 1H), 6.38 (s, 1H), 6.05 (bs, 1H), 5.55-5.37 (m, 2H), 5.32 (s, 1H), 5.23 (s, 1H), 4.68 (s, 36H), 4.52-4.31 (m, 2H), 4.15 (s, 1H), 4.00 (t, J=8.2 Hz, 1H), 3.85-3.61 (m, 3H), 3.56 (t, J=8.2 Hz, 1H), 3.35 (s, 1H), 2.67 (s, 4H), 2.03-1.88 (m, 2H), 1.75-1.39 (m, 3H), 1.33 (s, 3H), 1.05 (s, 3H), 0.75 (dd, J1=8.2 Hz, J2=13.7 Hz, 6H). HRMS (ESI) m/z: calcd. for C75H87Cl2N9O26 [M+1]+ 1602.4660; found 1602.5256.

Example 17

Releasable TCO-Daptomycin

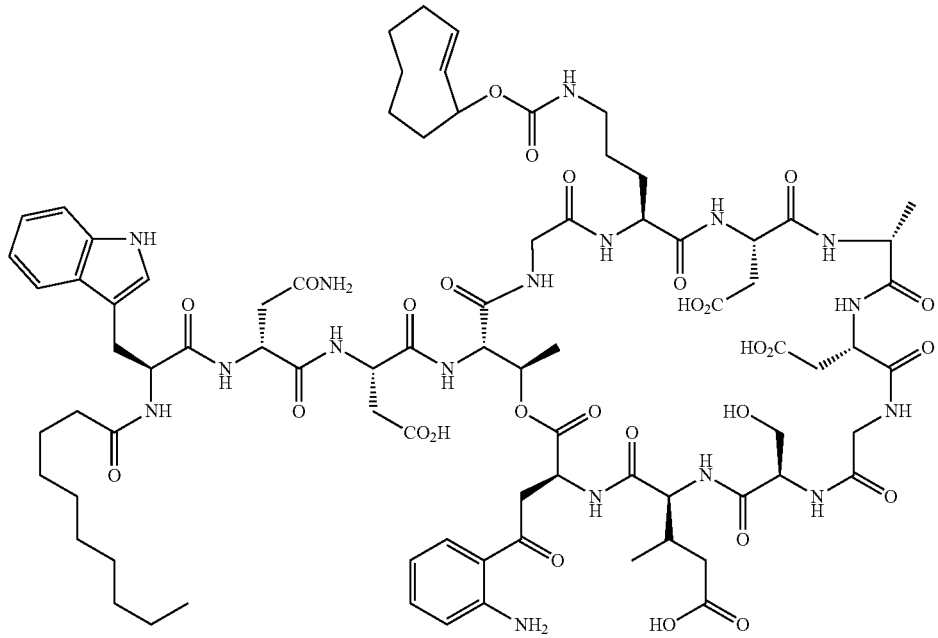 [SMILES: C=CCCCCCC(C)OC(=O)NCCC[C@@H]1NC(=O)CNC(=O)[C@@H](NC(=O)[C@H](CC(=O)O)NC(=O)[C@@H](CC(N)=O)NC(=O)[C@H](Cc2c[nH]c3ccccc23)NC(=O)CCCCCCCCC)[C@@H](C)OC(=O)[C@H](CC(=O)c2ccccc2N)NC(=O)[C@H](C(C)CC(=O)O)NC(=O)[C@@H](CO)NC(=O)CNC(=O)[C@H](CC(=O)O)NC(=O)[C@@H](C)NC(=O)[C@H](CC(=O)O)NC1=O]

Daptomycin (100 mg, 0.062 mmol) was dissolved in water (1 mL). A solution of (E)-cyclooct-2-enyl 4-nitrophenyl carbonate (36 mg, 0.123 mmol) in DMF (50 µL) was added, followed by Triethylamine (167 mg, 1.65 mmol). The reaction mixture was stirred at rt for 18 h. The title product was obtained as a white foam after HPLC purification using a semipreparative Phenomenex Luna 5u C18(2) column and a gradient of 10-65% $CH_3CN$ in $H_2O$. Yield=44 mg (40%). $^1H$ NMR ($CD_3OD$, 400 MHz) δ7.66 (bs, 2H), 7.60-7.46 (m, 2H), 7.39 (s, 1H), 7.25-7.11 (m, 2H), 7.02 (s, 1H), 6.96 (s, 1H), 6.83-6.78 (m, 1H), 6.56 (s, 1H), 6.00-5.68 (m, 4H), 5.68-5.57 (m, 1H), 5.54 (s, 1H), 5.51-5.26 (m, 8H), 5.14 (bs, 1H), 4.96 (bs, 1H), 4.67 (s, 1H), 4.64 (s, 1H), 4.58 (s, 1H), 4.14 (s, 1H), 3.88-3.79 (m, 2H), 3.78-3.71 (m, 1H), 3.59-3.43 (m, 2H), 3.19 (q, J=8.2 Hz, 7H), 2.95 (bs, 4H), 2.59-2.32 (m, 5H), 2.23-1.76 (m, 15H), 1.56-1.44 (m, 8H), 1.30 (t, J=8.1 Hz, 10H), 1.23-1.16 (m, 5H), 1.00-0.87 (m, 9H). MS (ESI) m/z: calcd. for $C_{75}H_{87}Cl_2N_9O_{26}$ [M+H+MeCN]$^+$ 1813.82; found 1813.80.

Example 18

Releasable TCO-Doxorubicin

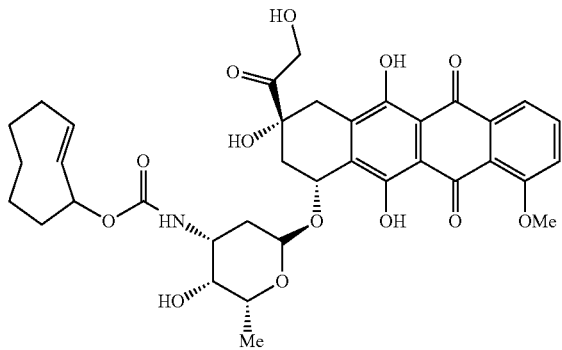

(E)-cyclooctene doxorubicin conjugate was synthesized as described by Versteegen, R. M. et. al., *Angew. Chem. Int. Ed.* 2013, 52, 14112-14116. The spectra from $^1H$ NMR ($CDCl_3$) matched the published data.

Example 19

Releasable TCO-Cyclic AMP

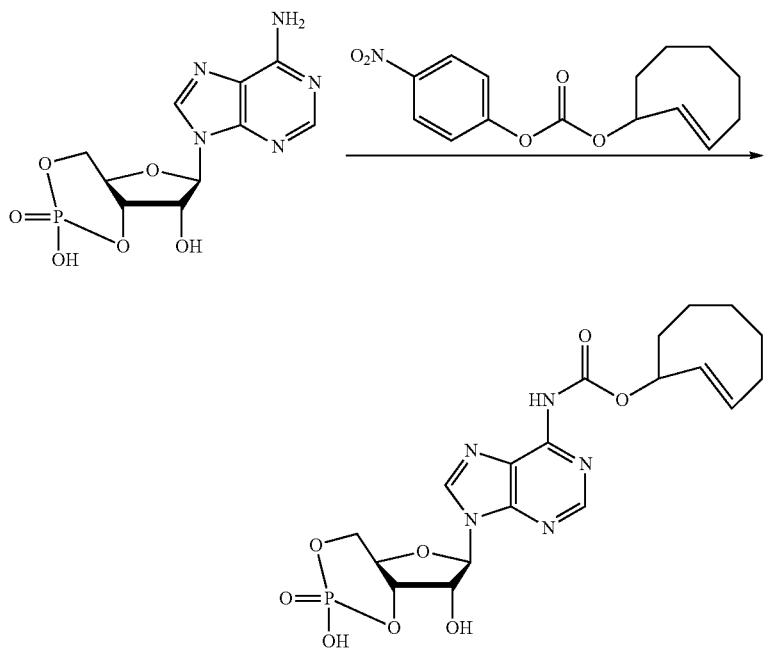

Cyclic AMP (80 mg, 0.243 mmol) and (E)-cyclooct-2-enyl 4-nitrophenyl carbonate (142 mg, 0.486 mmol) were dissolved in anhydrous DMF (8 mL). 4-Dimethylaminopyridine (238 mg, 1.94 mmol) was added and the reaction mixture was stirred at 30° C. for 18 h. The solvent was removed under high vacuum and the title product was obtained as a white foam after preparative column chromatography using 15% MeOH in $CH_2Cl_2$ as a mobile phase. Yield=45 mg (38%). $^1H$ NMR ($CDCl_3$, 400 MHz) δ7.61 (s, 1H), 7.57-7.41 (m, 2H), 7.19 (bs, 1H), 7.03 (s, 1H), 6.81 (bs, 1H), 6.44 (s, 1H), 6.38 (s, 1H), 6.06 (bs, 1H), 5.53-5.39 (m, 2H), 5.32 (s, 2H), 5.24 (s, 1H), 4.48 (bs, 2H), 4.16 (s, 1H), 4.00 (t, J=6.8 Hz, 1H), 3.83-3.61 (m, 3H), 3.60-3.50 (m, 1H), 3.35 (s, 1H), 2.68 (s, 4H), 2.03-1.90 (m, 2H), 1.75-1.40 (m, 3H), 1.33 (s, 3H), 1.05 (s, 3H), 0.74 (dd, J1=8.2 Hz, J2=13.6 Hz, 6H). HRMS (ESI) m/z: calcd. for $C_{19}H_{25}N_5O_8P$ [M+1]$^+$482.1441; found 482.1461.

Example 20

Releasable TCO-Compound 3

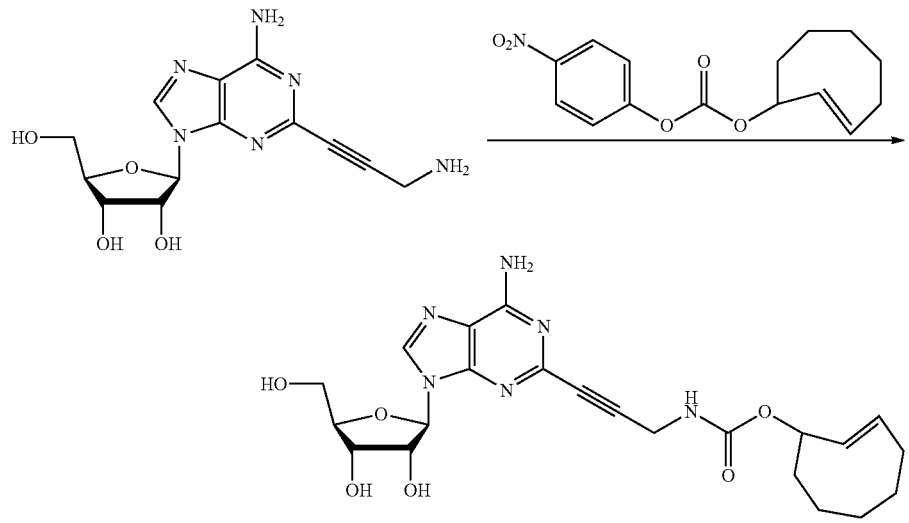

Compound 3 (132 mg, 0.413 mmol) and (E)-cyclooct-2-enyl 4-nitrophenyl carbonate (80 mg, 0.275 mmol) were dissolved in anhydrous DMF (5 mL). Triethylamine (167 mg, 1.65 mmol) was added and the reaction mixture was stirred at rt for 18 h. The solvent was removed under high vacuum and the title product was obtained as a white foam after preparative column chromatography using 10% MeOH in $CH_2Cl_2$ as a mobile phase. Yield=70 mg (36%). $^1$H NMR ($CD_3OD$, 400 MHz) δ8.28 (s, 1H), 5.93 (d, J=6.9 Hz, 1H), 5.89-5.78 (m, 1H), 5.54 (bs, 1H), 5.28 (bs, 1H), 4.73 (t, J=5.5 Hz, 1H), 4.37-4.31 (m, 1H), 4.23-4.13 (m, 3H), 3.92 (d, J=10.9 Hz, 1H), 3.73 (d, J=12.3 Hz, 1H), 3.65-3.40 (m, 1H), 3.35 (s, 1H), 3.31 (s, 1H), 2.47-2.30 (m, 1H), 2.10-1.75 (m, 4H), 1.75-1.57 (m, 2H), 1.53 (m, 1H), 1.26 (bs, 1H), 1.18-1.06 (m, 2H), 0.91-0.74 (m, 1H). HRMS (ESI) m/z: calcd. for $C_{22}H_{28}N_6O_6$ $[M+1]^+$473.2149; found 473.2117.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for selectively delivering an effective amount of a therapeutic or diagnostic agent to a first location of a targeted organ or tissue in a patient, comprising the steps of:
   (a) administering to the patient at the first location of the targeted organ or tissue a support composition comprising a biocompatible support and a first binding agent linked to the biocompatible support via a first linker, wherein the biocompatible support comprises at least one of a hydrogel, a polymer matrix, a metal, a ceramic, or a plastic, and the first binding agent comprises trans-cyclooctene or tetrazine;
   (b) administering to the patient a bioactive composition comprising a therapeutic or diagnostic agent, a second binding agent comprising trans-cyclooctene or tetrazine complementary to the first binding agent, and a releasable linker linking the therapeutic or diagnostic agent and the second binding agent, such that the first and second binding agent bind to one another upon contact; and
   (c) releasing the therapeutic or diagnostic agent, thereby delivering the therapeutic or diagnostic agent to the first location of the targeted organ or tissue.

2. The method of claim 1, wherein the first binding agent is trans-cyclooctene and the second binding agent is tetrazine.

3. The method of claim 1, wherein the second binding agent is 1,2,4,5-tetrazine.

4. The method of claim 1, wherein the support composition is:

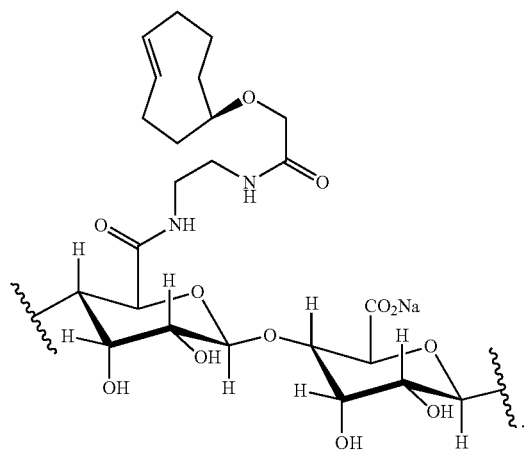

5. The method of claim 1, wherein the support composition is:

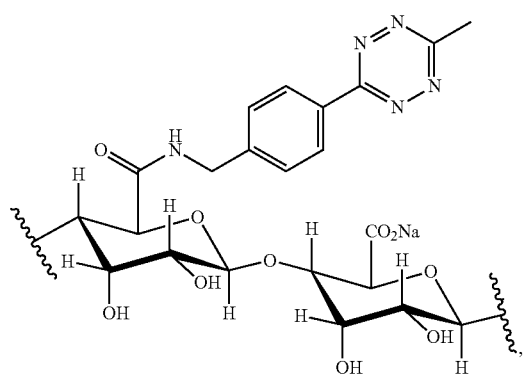

and the bioactive composition is selected from the group consisting of:

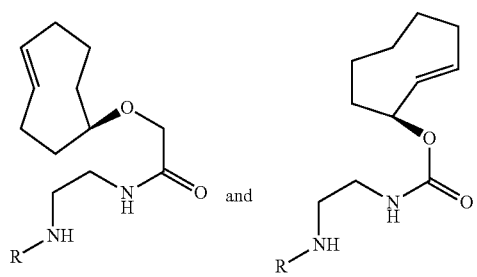

wherein R is selected from the group consisting of the therapeutic agent and the diagnostic agent.

6. The method of claim 1, wherein the targeted organ or tissue is bone.

7. The method of claim 1, wherein the concentration of the therapeutic or diagnostic agent at the first location of the targeted organ or tissue is greater than the concentration elsewhere in the patient.

8. The method of claim 1, wherein the therapeutic agent is vancomycin.

9. The method of claim 1, wherein the first binding agent and the first linker or second binding agent and the releasable linker together have the structure of:

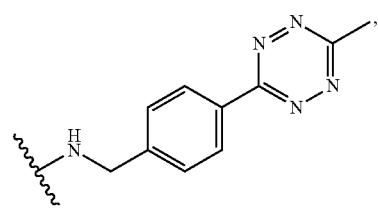

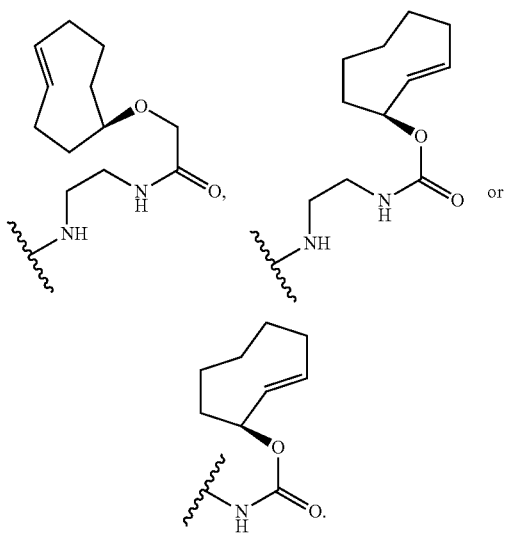

10. The method of claim 9, wherein the biocompatible support is selected from the group consisting of alginate, cellulose, chitosan, chitin, hyaluronic acid, chondroitin sulfate and heparin.

11. The method of claim 1, wherein the first binding agent and the first linker or second binding agent and the releasable linker together have the structure of:

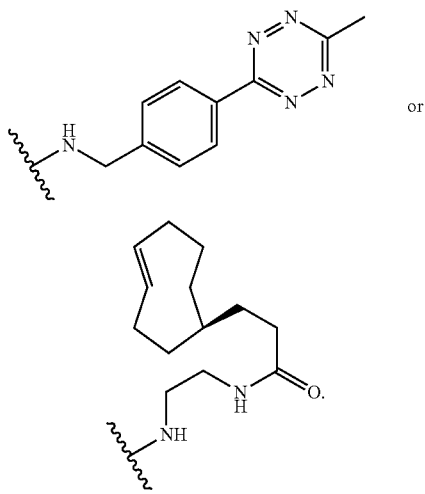

12. The method of claim 1, wherein the first binding agent and the first linker or second binding agent and the releasable linker together have the structure of:

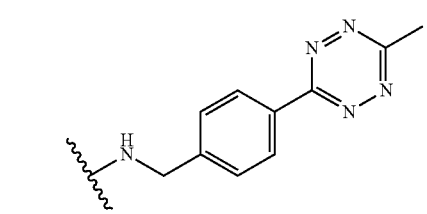

-continued

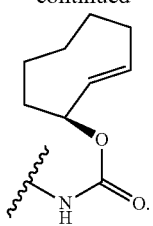

13. The method of claim 1, wherein the support composition having the structure of:

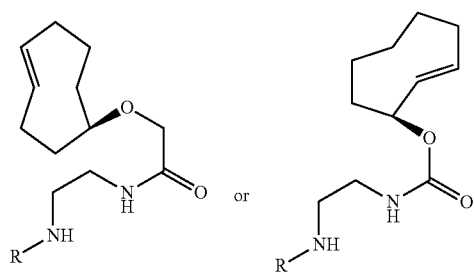

wherein R is the biocompatible support.

14. The method of claim 1, wherein the biocompatible support comprises a hydrogel.

15. The method of claim 1, wherein the biocompatible support is selected from the group consisting of polysaccharide hydrogels, alginate, cellulose, hyaluronic acid, chitosan, chitin, hyaluronic acid, chondroitin sulfate, and heparin.

16. The method of claim 1, wherein the biocompatible support is selected from the group consisting of alginate, chitin, hyaluronic acid, chitosan, and agarose.

17. The method of claim 1, wherein the biocompatible support is selected from the group consisting of collagen, gelatin, elastin and elastin-like polypeptides, albumin, fibrin, poly(gamma-glutamic acid), poly(L-lysine), poly(L-glutamic acid), and poly(aspartic acid).

18. The method of claim 1, wherein the support composition has the structure:

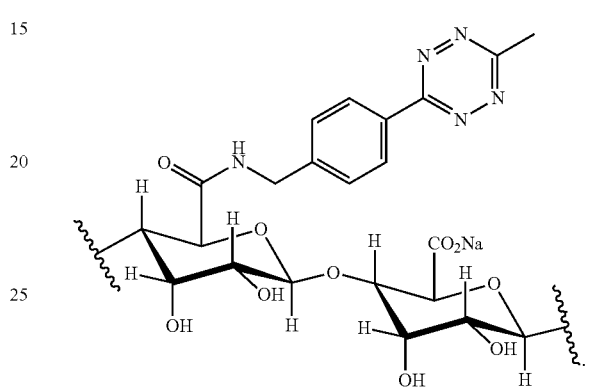

19. The method of claim 1, wherein the biocompatible support comprises a polymer matrix.

* * * * *